United States Patent
Liu et al.

(10) Patent No.: US 12,421,305 B2
(45) Date of Patent: Sep. 23, 2025

(54) ANTIBODY FOR ENRICHMENT OF CELLS

(71) Applicant: CHO PHARMA, INC., Taipei (TW)

(72) Inventors: Ying-Chih Liu, Taipei (TW); Chien-Yu Chen, Taipei (TW); Ju-Mei Li, Taipei (TW)

(73) Assignee: CHO PHARMA, INC., Taipei (TW)

( * ) Notice: Subject to any disclaimer, the term of this patent is extended or adjusted under 35 U.S.C. 154(b) by 0 days.

(21) Appl. No.: 17/538,334

(22) Filed: Nov. 30, 2021

(65) Prior Publication Data

US 2022/0169710 A1   Jun. 2, 2022

Related U.S. Application Data

(60) Provisional application No. 63/119,345, filed on Nov. 30, 2020.

(51) Int. Cl.
| | |
|---|---|
| C07K 16/18 | (2006.01) |
| A61K 40/11 | (2025.01) |
| A61K 40/31 | (2025.01) |
| A61K 40/42 | (2025.01) |
| C12N 5/0783 | (2010.01) |

(52) U.S. Cl.
CPC ............ *C07K 16/18* (2013.01); *A61K 40/11* (2025.01); *A61K 40/31* (2025.01); *A61K 40/42* (2025.01); *C12N 5/0636* (2013.01); *A61K 2239/48* (2023.05); *C07K 2317/41* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen | A61P 19/02 |
| | | | 435/69.6 |
| 6,586,239 B1 * | 7/2003 | Mi | C12N 5/0622 |
| | | | 435/395 |
| 10,598,669 B2 | 3/2020 | Fandl et al. | |
| 2016/0102151 A1 | 4/2016 | Wong et al. | |
| 2016/0280794 A1 * | 9/2016 | Wong | C12P 21/005 |
| 2016/0369002 A1 | 12/2016 | Gauthier et al. | |
| 2017/0283489 A1 | 10/2017 | Bosio et al. | |
| 2018/0142212 A1 | 5/2018 | Bernstein et al. | |
| 2018/0185417 A1 | 7/2018 | Joly et al. | |
| 2018/0208895 A1 | 7/2018 | Cavazzana-Calvo et al. | |
| 2018/0291109 A1 * | 10/2018 | Lin | A61P 35/00 |
| 2019/0077850 A1 | 3/2019 | Ingber et al. | |
| 2019/0107537 A1 | 4/2019 | Chaudhary | |
| 2019/0389941 A1 | 12/2019 | Block et al. | |
| 2020/0062861 A1 | 2/2020 | Yu et al. | |
| 2020/0064337 A1 | 2/2020 | Park et al. | |
| 2020/0276308 A1 | 9/2020 | Chen | |

FOREIGN PATENT DOCUMENTS

| | | |
|---|---|---|
| WO | 2015184002 A1 | 12/2015 |
| WO | 2016123591 A2 | 8/2016 |
| WO | 2018018047 A2 | 1/2018 |
| WO | 2018146297 A1 | 8/2018 |
| WO | 2019027850 A1 | 2/2019 |

OTHER PUBLICATIONS

Neurauter, Axl A., et al. "Cell isolation and expansion using Dynabeads®." Cell Separation: Fundamentals, Analytical and Preparative Methods (2007): 41-73. (Year: 2007).*
Li, Tiezheng, et al. "Modulating IgG effector function by Fc glycan engineering." Proceedings of the National Academy of Sciences 114.13 (2017): 3485-3490 (Year: 2017).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Search Report issued in the corresponding PCT application No. PCT/US2021/061181 mailed Mar. 30, 2022.
Written Opinion issued in the corresponding PCT application No. PCT/US2021/061181 mailed Mar. 30, 2022.
Office Action with Search Report dated Apr. 26, 2023.
European Search Report (ESR) issued in corresponding EP application No. 21899222.0 on Mar. 18, 2025.

* cited by examiner

*Primary Examiner* — Zachariah Lucas
*Assistant Examiner* — Lia E Taylor
(74) *Attorney, Agent, or Firm* — LADAS & PARRY LLP

(57) ABSTRACT

The present disclosure relates to a modified antibody or antigen-binding fragment thereof that specifically binds to SSEA4; especially with a glycol-engineered N-glycan. The present disclosure also relates to a method for enrichment of cells with the modified antibody or antigen-binding fragment thereof.

7 Claims, 23 Drawing Sheets

Specification includes a Sequence Listing.

ANTIBODY FOR ENRICHMENT OF CELLS

CROSS-REFERENCE TO RELATED APPLICATIONS

This application claims priority from U.S. 63/119,345 filed 30 Nov. 2020, the contents of which are incorporated herein by reference in their entirety.

FIELD OF THE DISCLOSURE

The present disclosure relates to an antibody or antigen-binding fragment thereof, which is specific to stage-specific embryonic antigen 4 (SSEA4) for enrichment immune cells.

BACKGROUND OF THE DISCLOSURE

Cell therapy, also known as cellular therapy, is developed as a powerful strategy to treat many diseases such as cancers, genetic diseases, and autoimmune disorders. The therapy comprises introducing desired cells into a patient in need of such treatment for exerting a medicinal effect. Among various cells utilized in cell therapy, immune cells play an important role in view of their outstanding success in cancer treatment. For example, transplanting T-cells is capable of inhibiting cancer growth via cell-mediated immunity. Enrichment of desired immune cells is essential in the field of cell therapy. Conventional methods for selecting desired immune cells among peripheral blood mononuclear cells (PBMCs) usually utilize an antibody specific to a unique antigen located on the surface of the desired immune cells. For example, an anti-CD56 antibody is applied in selecting natural killer cells which express CD56 antigen on the cell surface. However, almost natural killer cells express CD56 antigen, and the conventional method fails to select sub-groups among killer cells.

Thus, there is need for developing a novel approach to enrichment of cells.

SUMMARY OF THE DISCLOSURE

The present disclosure relates to a method for enrichment of cells with the modified antibody or antigen-binding fragment thereof. The present disclosure also provides an antibody or antigen-binding fragment thereof that specifically binds to an epitope in an antigen or a fragment thereof.

In one aspect, the present disclosure provides an the antibody or antigen-binding fragment thereof comprising complementarity determining regions (CDRs) of a heavy chain variable region and CDRs of a light chain variable region, wherein the CDRs of the heavy chain variable region comprises CDRH1, CDRH2 and CDRH3 regions, and the CDRs of the light chain variable region comprises CDRL1, CDRL2 and CDRL3 regions, and wherein:
 the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 3; and
 the CDRL1 region comprises the amino acid sequence of SEQ ID NO: 4; the CDRL2 region comprises the amino acid sequence of SEQ ID NO: 5; the CDRL3 region comprises the amino acid sequence of SEQ ID NO: 6;
 or
 the CDRH1 region comprises the amino acid sequence of SEQ ID NO: 25; the CDRH2 region comprises the amino acid sequence of SEQ ID NO: 26; the CDRH3 region comprises the amino acid sequence of SEQ ID NO: 27; and
 the CDRL1 region comprises the amino acid sequence of SEQ ID NO: 28; the CDRL2 region comprises the amino acid sequence of SEQ ID NO: 29; the CDRL3 region comprises the amino acid sequence of SEQ ID NO: 30;
 or
 the CDRH1 region comprises the amino acid sequence of SEQ ID NO: 25; the CDRH2 region comprises the amino acid sequence of SEQ ID NO: 31; the CDRH3 region comprises the amino acid sequence of SEQ ID NO: 32; and
 the CDRL1 region comprises the amino acid sequence of SEQ ID NO: 28; the CDRL2 region comprises the amino acid sequence of SEQ ID NO: 29; the CDRL3 region comprises the amino acid sequence of SEQ ID NO: 30.

In one aspect, the present disclosure provides an antibody or antigen-binding fragment thereof or Fc-fused antigen-binding fragment thereof comprising the CDRs as disclosed herein.

In one embodiment of the disclosure, the CDRH1 region comprises the amino acid sequence of SEQ ID NO: 7, 13 or 14.

In one embodiment of the disclosure, the CDRH2 region comprises the amino acid sequence of SEQ ID NO: 8 or 15.

In one embodiment of the disclosure, the CDRH3 region comprises the amino acid sequence of SEQ ID NO: 9, 16, 17, or 18.

In one embodiment of the disclosure, the CDRL1 region comprises the amino acid sequence of SEQ ID NO: 10 or 19.

In one embodiment of the disclosure, the CDRL2 region comprises the amino acid sequence of SEQ ID NO: 11, 20 or 21.

In one embodiment of the disclosure, the CDRL3 region comprises the amino acid sequence of SEQ ID NO: 12 or 22.

In one embodiment of the disclosure, the antibody or antigen-binding fragment thereof comprises the CDRH1 region being SEQ ID NO: 13, the CDRH2 region being SEQ ID NO: 8, the CDRH3 region being SEQ ID NO: 9, the CDRL1 region being SEQ ID NO: 10, the CDRL2 region being SEQ ID NO: 20 and the CDRL3 region being SEQ ID NO: 12.

In one embodiment of the disclosure, the antibody or antigen-binding fragment thereof comprises the CDRH1 region being SEQ ID NO: 13, the CDRH2 region SEQ ID NO: 15, the CDRH3 region being SEQ ID NO: 9, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 13, the CDRH2 region being SEQ ID NO: 8, the CDRH3 region being SEQ ID NO: 16, the CDRL1 region being SEQ ID NO: 10, the to CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 14, the CDRH2 region being SEQ ID NO: 8, the CDRH3 region being SEQ ID NO: 17, the CDRL1 region being SEQ ID NO: 10, the CDRL2 region being SEQ ID NO: 21 and the CDRL3 region being SEQ ID NO: 12.

In one embodiment of the disclosure, the antibody or antigen-binding fragment thereof comprises the CDRH1 region being SEQ ID NO: 14, the CDRH2 region being SEQ ID NO: 8, the CDRH3 region being SEQ ID NO: 18, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 15, the CDRH3 region being SEQ ID NO: 9, the CDRL1 region being SEQ ID NO: 10, the CDRL2 region being SEQ ID NO: 20 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 15, the CDRH3 region being SEQ ID NO: 17, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 8, the CDRH3 region being SEQ ID NO: 16, the CDRL1 region being SEQ ID NO: 10, the CDRL2 region being SEQ ID NO: 20 and the CDRL3 region being SEQ ID NO: 12.

In one embodiment of the disclosure, the antibody or antigen-binding fragment thereof comprises a heavy chain variable region comprising the amino acid sequence of SEQ ID NO: 23 or a substantially similar sequence thereof and a light chain variable region comprising the amino acid sequence of SEQ ID NO: 24 or a substantially similar sequence thereof.

In one embodiment of the disclosure, the antigen-binding fragment is a single-chain FAT (scFv) molecule comprising the amino acid sequence of SEQ ID NO: 37.

In one embodiment of the disclosure, the antigen-binding fragment is fused to an Fc region having the amino acid sequence of SEQ ID NO: 38.

In one embodiment of the disclosure, the antibody or antigen-binding fragment thereof further comprises a heavy chain variable region comprising the amino acid sequence of SEQ ID NO: 33 or a substantially similar sequence thereof; and a light chain variable region comprising the amino acid sequence of SEQ ID NO: 34 or a substantially similar sequence thereof.

In one embodiment of the disclosure, the antibody or antigen-binding fragment thereof further comprises a heavy chain variable region comprising the amino acid sequence of SEQ ID NO: 35 or a substantially similar sequence thereof; and a light chain variable region comprising the amino acid sequence of SEQ ID NO: 36 or a substantially similar sequence thereof.

In one embodiment of the disclosure, the antibody comprises an Fc region or the antigen-binding fragment is fused to an Fc region, and the antibody or antigen-binding fragment thereof has an N-glycan on the Fc region, and the N-glycan is selected from the group consisting of $Man_5GlcNAc_2$ (Man5), $GlcNAc_2Man_3GlcNAc_2(Fuc)$ (G0F), $GalGlcNAc_2Man_3GlcNAc_2(Fuc)$ (G1F), $Gal_2GlcNAc_2Man_3GlcNAc_2(Fuc)$ (G2F), $Sia_2(\alpha 2\text{-}3)Gal_2GlcNAc_2Man_3GlcNAc_2(Fuc)$ (G2S2F (alpha 2,3 linkage)), $Sia_2(\alpha 2\text{-}6)Gal_2GlcNAc_2Man_3GlcNAc_2(Fuc)$ (G2S2F (alpha 2,6 linkage)), $GlcNAc_2Man_3GlcNAc_2$ (G0), $Gal_2GlcNAc_2Man_3GlcNAc_2$ (G2), $Sia_2(\alpha 2\text{-}3)Gal_2GlcNAc_2Man_3GlcNAc_2$ (G2S2 (alpha 2,3 linkage)), and $Sia_2(\alpha 2\text{-}6)Gal_2GlcNAc_2Man_3GlcNAc_2$ (G2S2 (alpha 2,6 linkage)).

In one embodiment of the disclosure, the antibody or antigen-binding fragment thereof comprises a heavy chain variable region comprising the amino acid sequence of SEQ ID NO: 23 and a light chain variable region comprising the amino acid sequence of SEQ ID NO: 24, and the N-glycan is selected from the group consisting of Man5, G0F, G1F and G2F.

In one embodiment of the disclosure, the N-glycan is selected from the group consisting of G0F, G2F, G2S2F (alpha 2,3 linkage), G2S2F (alpha 2,6 linkage), G0, G2, G2S2 (alpha 2,3 linkage), and G2S2 (alpha 2,6 linkage), and a plurality of the antibodies or antigen-binding fragment thereof are provided in a population, and more than about 90% of the population has the same N-glycan.

The present disclosure also provides a kit for enrichment of cells comprising an antibody or antigen-binding fragment thereof, wherein the antibody comprises an Fc region or the antigen-binding fragment is fused to an Fc region, and the antibody or antigen-binding fragment thereof is glycoengineered on the Fc region; and a support for immorbilizing the antibody or antigen-binding fragment thereof.

In one aspect, the present disclosure provides a kit for enrichment of cells comprising an antibody or antigen-binding fragment thereof, wherein the antibody comprises an Fc region, or the antigen-binding fragment is fused to an Fc region to form an Fc-fused antigen-binding fragment, and the antibody or Fc-fused antigen-binding fragment thereof is glycoengineered on the Fc region; and a support for immobilizing the antibody or antigen-binding fragment thereof.

In some embodiments, the kit comprises the antibody or antigen-binding fragment thereof as described herein.

In one embodiment of the disclosure, the support is a magnetic bead.

In one embodiment of the disclosure, the kit further comprises an antigen linked to the support.

In a further embodiment, the antigen is SSEA4. In one embodiment, the antigen binds to the antibody or antigen-binding fragment thereof.

In one embodiment of the disclosure, wherein the antibody or antigen-binding fragment is an anti-SSEA4 antibody or SSEA4-binding fragment.

In another aspect, the present disclosure also provides a method for enrichment of cells comprising:
  contacting a pool of cells with an antibody or antigen-binding fragment thereof, wherein the antibody comprises an Fc region or the antigen-binding fragment is fused to an Fc region to form an Fc-fused antigen-binding fragment, and the antibody or Fc-fused antigen-binding fragment thereof is glycoengineered on the Fc region; and
  isolating cells binding to the antibody or Fc-fused antigen-binding fragment thereof from the pool.

In another aspect, the present disclosure also provides a method for enrichment of cells comprising:
  contacting a pool of cells with an antibody or antigen-binding fragment thereof, wherein the antibody comprises an Fc region, or the antigen-binding fragment is fused to an Fc region to form an Fc-fused antigen-binding fragment, and the antibody or Fc-fused antigen-binding fragment thereof is glycoengineered on the Fc region; and
  isolating cells binding to the antibody or Fc-fused antigen-binding fragment thereof from the pool.

In one embodiment of the disclosure, the method is for enrichment of immune cells.

In one embodiment of the disclosure, the pool of cells is peripheral blood mononuclear cells. In one more preferred embodiment of the disclosure, the peripheral blood mononuclear cells are selected from the group consisting of natural killer cells, natural killer T cells, macrophages, monocytes and B cells.

In one embodiment of the disclosure, the antibody or antigen-binding fragment thereof is immobilized on a support.

In one embodiment of the disclosure, the antibody has a fragment antigen binding region (Fab region) or Fc-fused antigen-binding fragment has the antigen-binding fragment, and the Fab region or the antigen-binding fragment is immobilized on the support, and the isolated cells bind to the Fc region.

In one embodiment of the disclosure, the Fab region or the antigen-binding fragment binds to SSEA4 linked on the support.

In one embodiment of the disclosure, the support is a magnetic bead.

In one embodiment of the disclosure, the method further comprises:
    isolating cells that fail to bind to the antibody or Fc-fused antigen-binding fragment thereof from the pool.

In one embodiment of the disclosure, the cells that fail to bind to the antibody or Fc-fused antigen-binding fragment are T cells.

In one embodiment of the disclosure, the antibody or antigen-binding fragment is an anti-SSEA4 antibody or SSEA4-binding fragment.

In an embodiment, more than about 90% of the cells that fail to bind to the antibody or Fc-fused antigen-binding fragment are T cells.

In one embodiment of the disclosure, the method comprises the antibody or antigen-binding fragment thereof as described herein.

The present disclosure is described in detail in the following sections. Other characteristics, purposes and advantages of the present disclosure can be found in the detailed description and claims.

BRIEF DESCRIPTION OF THE DRAWINGS

FIG. 3 (A): CDRH1. FIG. 3 (B): CDRH2. FIG. 3 (C): CDRH3. FIG. 3 (D): CDRL1. FIG. 3 (E): CDRL2. FIG. 3 (F): CDRL3.

FIG. 4 (A): Q32 of CDRH1. FIG. 4 (B): Y35 of CDHR1. FIG. 4 (C): I51 of CDHR2. FIG. 4 (D): W52 of CDRH2. FIG. 4 (E): V98 of CDRH3. FIG. 4 (F): N105 of CDRH3.

FIG. 5 (A): Y31 of CDRL1. FIG. 5 (B): D49 of CDRL2. FIG. 5 (C): T50 of CDRL2. FIG. 5 (D): F88 of CDRL3. FIG. 5 (E): Q89 of CDRL3. FIG. 5 (F): G90 of CDRL3. FIG. 5 (G): Y93 of CDRL3. FIG. 5 (H): P94 of CDRL3. FIG. 5 (I): L95 of CDRL3.

FIG. 12 (B) shows the beads-enriched fraction of immune cells enrichment using different antibodies anti-SSEA4-G2S2 (α2,6) and anti-SSEA4(3)-G2S2 (α2,6).

FIG. 18 (B) shows the CAR (anti-CD19 or anti-SSEA4) expression efficiency. FIG. 18 (C) shows the cytotoxicity activities of individual CAR-T cells prepared by each cell population ($CAR^+$ FT T cells or $CAR^+$ Ctrl T cells).

DETAILED DESCRIPTION OF THE DISCLOSURE

Figure 1:
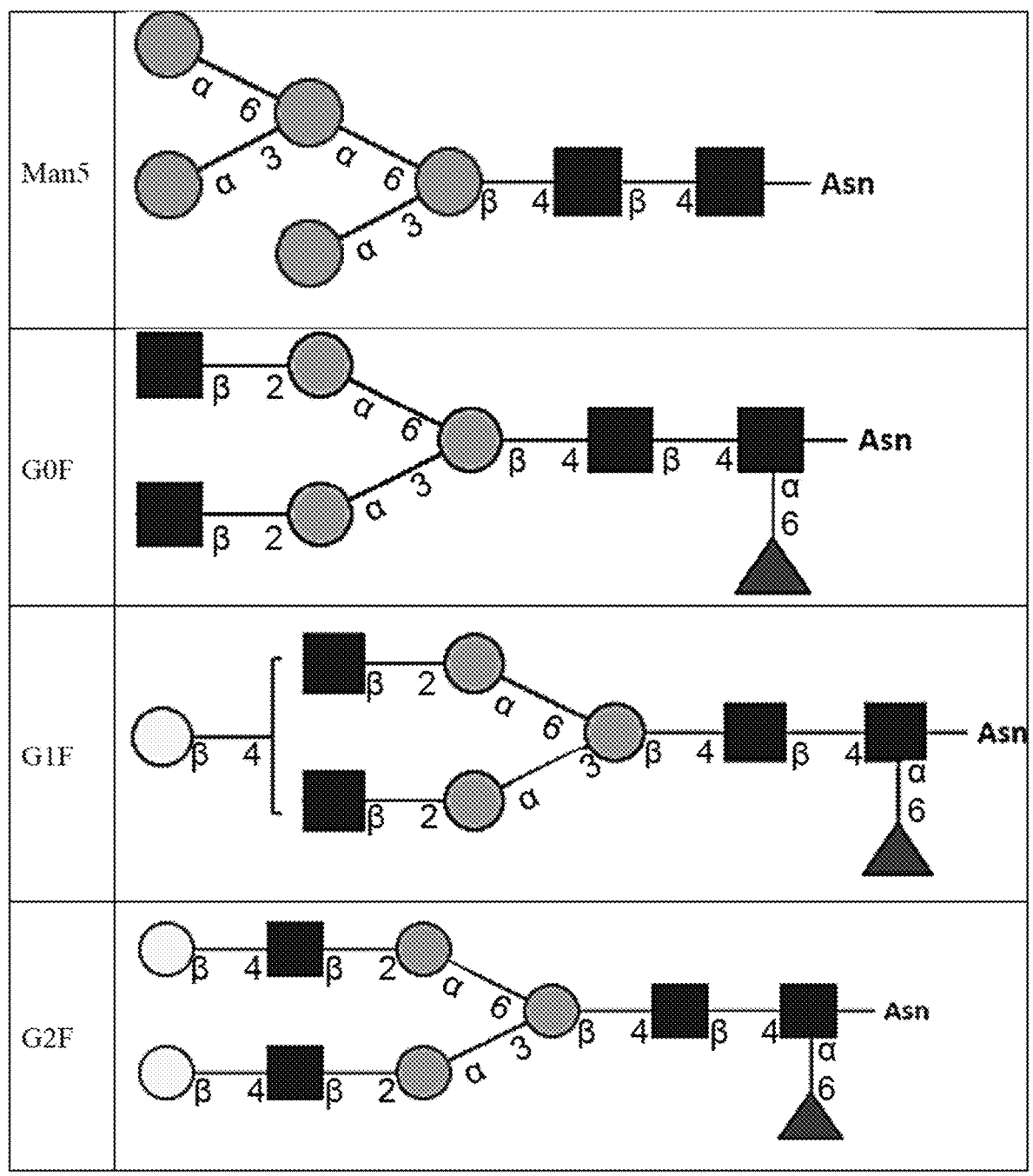
FIG. 1 shows the schematic structures of the N-glycans.
Figure 1:
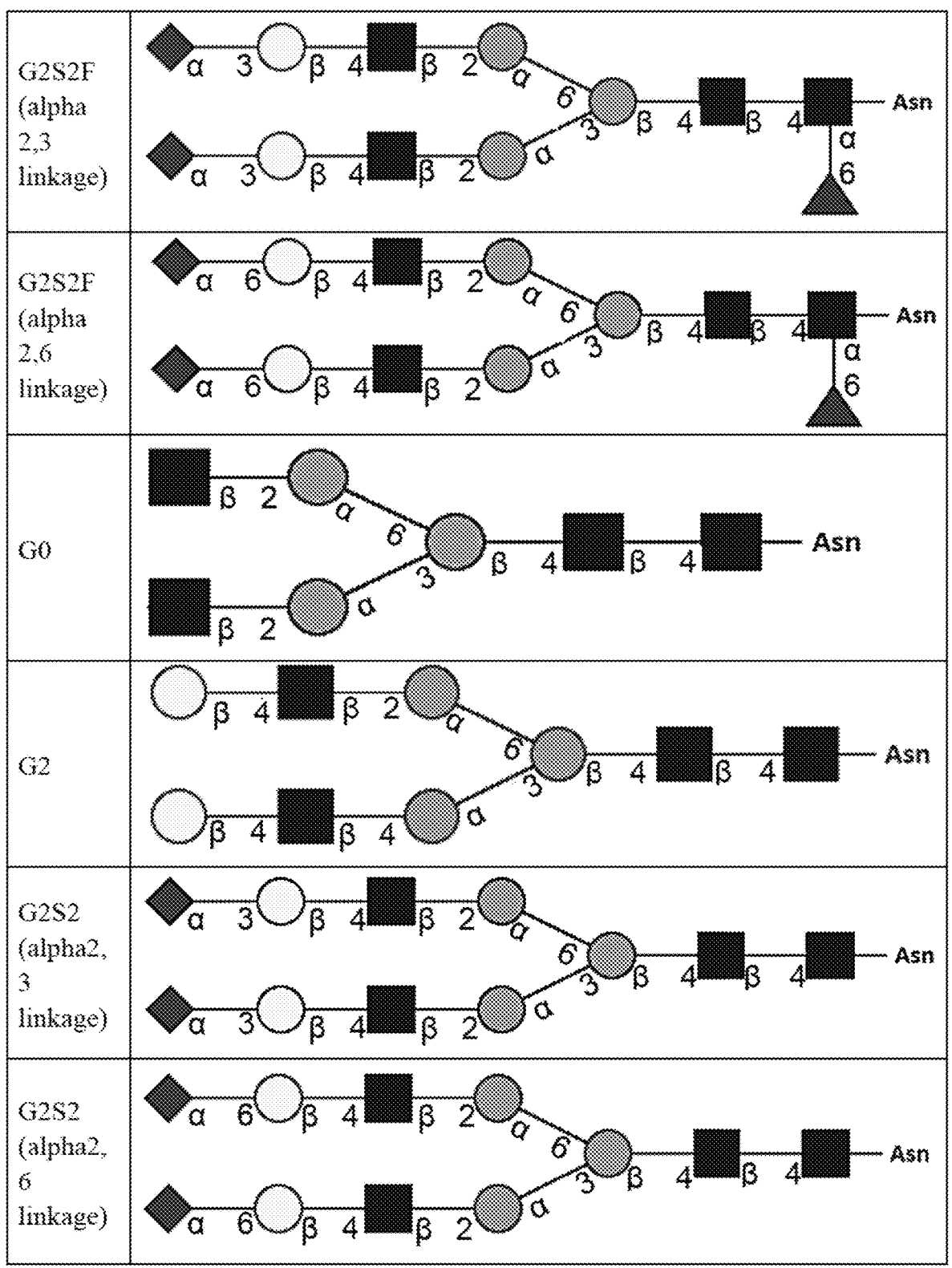

In the description that follows, a number of terms are used and the following definitions are provided to facilitate understanding of the claimed subject matter. Terms that are not expressly defined herein are used in accordance with their plain and ordinary meanings.

Unless otherwise specified, "a" or "an" means "one or more."

As used herein, the term "epitope" refers to the site on the antigen to which an antibody binds.

The term "antibody", as used herein, means any antigen-binding molecule or molecular complex comprising at least one complementarity determining region (CDR) that specifically binds to or interacts with a particular antigen (e.g., SSEA4). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-SSEA4 antibody (or antigen-binding portion thereof) may be identical to the human germline sequences, or may be naturally or artificially modified. An amino acid consensus sequence may be defined based on a side-by-side analysis of two or more CDRs.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

The present disclosure provides an antibody or antigen-binding fragment thereof that specifically binds to an epitope in SSEA4 or a fragment thereof. In one aspect, the present disclosure provides an antibody or antigen-binding fragment thereof or Fc-fused antigen-binding fragment thereof that specifically binds to an epitope in SSEA4 or a fragment thereof.

In one embodiment, the antibody or antigen-binding fragment thereof (anti-SSEA4) comprises complementarity determining regions (CDRs) of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and wherein:

the CDRH1 region comprises the amino acid sequence of SEQ ID NO: 1 (S-$X_{a1}$-GVY, $X_{a1}$ being Q, C, D, E, F, G, H, I, L, M, N, P, R, S, T, V, W, or Y); preferably, the CDRH1 region comprises the amino acid sequence of SEQ ID NO: 7 (SQGVY), SEQ ID NO: 13 (SIGVY) or SEQ ID NO: 14 (STGVY);

the CDRH2 region comprises the amino acid sequence of SEQ ID NO: 2 (A-$X_{a2}$-WAGGSTNYNSALMS, $X_{a2}$ being A, R, N, D, C, E, Q, G, H, I, L, K, M, F, S, T, or V); preferably, the CDRH2 region comprises the amino acid sequence of SEQ ID NO: 8 (AIWAGGSTNYN-SALMS) or SEQ ID NO: 15 (AGWAGGSTNYN-SALMS);

the CDRH3 region comprises the amino acid sequence of SEQ ID NO: 3 ($X_{a3}$-DGYRGY-$X_{a4}$-MDY, $X_{a3}$ being V, I, P or S, Xaa being N, T, G or Q); preferably, the CDRH3 region comprises the amino acid sequence of SEQ ID NO: SEQ ID NO: 9 (VDGYRGYNMDY), SEQ ID NO: 16 (IDGYRGYNMDY), SEQ ID NO: 17 (VDGYRGYGMDY) and SEQ ID NO: 18 (VDGYR-GYQMDY);

the CDRL1 region comprises the amino acid sequence of SEQ ID NO: 4 (SSVSX$_{a5}$, $X_{a5}$ being Y or H); preferably, the CDRL1 region comprises the amino acid sequence of SEQ ID NO: 10 (SSVSY) or SEQ ID NO: 19 (SSVSH);

the CDRL2 region comprises the amino acid sequence of SEQ ID NO: 5 (D-$X_{a6}$-S, $X_{a6}$ being A, R, N, C, Q, G, H, I, L, K, M, F, S, T, Y, or V); preferably, the CDRL2 region comprises the amino acid sequence of SEQ ID NO: 11 (DTS), SEQ ID NO: 20 (DHS) or SEQ ID NO: 21 (DVS); and the CDRL3 region comprises the amino acid sequence of SEQ ID NO: 6 (FQGSG-$X_{a7}$-PL, $X_{a7}$ being Y or I); preferably, the CDRL3 region comprises the amino acid sequence of SEQ ID NO: 12 (FQGSGYPL) or SEQ ID NO: 22 (FQGSGIPL).

Particularly, the antibody or antigen-binding fragment thereof (anti-SSEA4(2)) comprises:

the CDRH1 region comprises the amino acid sequence of SEQ ID NO: 25 (GFSLKNYGVS); the CDRH2 region comprises the amino acid sequence of SEQ ID NO: 26 (VIWGDGSTNYHSTLRS); the CDRH3 region comprises the amino acid sequence of SEQ ID NO: 27 (PGRGYAMDY); and the CDRL1 region comprises the amino acid sequence of SEQ ID NO: 28 (SASSSVSYMH); the CDRL2 region comprises the amino acid sequence of SEQ ID NO: 29 (YDTSKLTS); the CDRL3 region comprises the amino acid sequence of SEQ ID NO: 30 (FQGSGYPLT).

Particularly, the antibody or antigen-binding fragment thereof (anti-SSEA4(3)) comprises:

the CDRH1 region comprises the amino acid sequence of SEQ ID NO: 25; the CDRH2 region comprises the amino acid sequence of SEQ ID NO: 31 (VIWGDG-STNYYADSVKG); the CDRH3 region comprises the amino acid sequence of SEQ ID NO: 32 (PGAG-YAMDY); and the CDRL1 region comprises the amino acid sequence of SEQ ID NO: 28; the CDRL2 region comprises the amino acid sequence of SEQ ID NO: 29; the CDRL3 region comprises the amino acid sequence of SEQ ID NO: 30.

The sequence listing is shown in Table 1.

TABLE 1

| SEQ ID NO: | Sequence | Description |
|---|---|---|
| 1 | S-$X_{a1}$-GVY, $X_{a1}$ being Q, C, D, E, F, G, H, I, L, M, N, P, R, S, T, V, W, or Y | anti-SSEA4 CDRH1 variant |
| 2 | A-$X_{a2}$-WAGGSTNYNSALMS, $X_{a2}$ being A, R, N, D, C, E, Q, G, H, I, L, K, M, F, S, T, or V | anti-SSEA4 CDRH2 variant |
| 3 | $X_{a3}$,-DGYRGY-$X_{a4}$-MDY, $X_{a3}$ being V, I, P or S, $X_{a4}$ being N, T, G or Q | anti-SSEA4 CDRH3 variant |

TABLE 1-continued

| SEQ ID NO: | Sequence | Description |
|---|---|---|
| 4 | SSVSX$_{a5}$, X$_{a5}$ being Y or H | anti-SSEA4 CDRL1 variant |
| 5 | D-X$_{a6}$-S, X$_{a6}$ being A, R, N, C, Q, G, H, I, L, K, M, F, S, T, Y, or V | anti-SSEA4 CDRL2 variant |
| 6 | FQGSG-X$_{a7}$-PL, X$_{a7}$ being Y or I | anti-SSEA4 CDRL3 variant |
| 7 | SQGVY | anti-SSEA4 CDRH1 wild type |
| 8 | AIWAGGSTNYNSALMS | anti-SSEA4 CDRH2 wild type |
| 9 | VDGYRGYNMDY | anti-SSEA4 CDRH3 wild type |
| 10 | SSVSY | anti-SSEA4 CDRL1 wild type |
| 11 | DTS | anti-SSEA4 CDRL2 wild type |
| 12 | FQGSGYPL | anti-SSEA4 CDRL3 wild type |
| 13 | SIGVY | anti-SSEA4 CDRH1 mutant |
| 14 | STGVY | anti-SSEA4 CDRH1 mutant |
| 15 | AGWAGGSTNYNSALMS | anti-SSEA4 CDRH2 mutant |
| 16 | IDGYRGYNMDY | anti-SSEA4 CDRH3 mutant |
| 17 | VDGYRGYGMDY | anti-SSEA4 CDRH3 mutant |
| 18 | VDGYRGYQMDY | anti-SSEA4 CDRH3 mutant |
| 19 | SSVSH | anti-SSEA4 CDRL1 mutant |
| 20 | DHS | anti-SSEA4 CDRL2 mutant |
| 21 | DVS | anti-SSEA4 CDRL2 mutant |
| 22 | FQGSGIPL | anti-SSEA4 CDRL3 mutant |
| 23 | QVQLQESGPGLVAPSETLSITCTVSGFSLSSQGVYWVRQPPGKGLEWLGAIWAGGSTNYNSALMSRLSISKDNSKSQVFLKMNSLTAADTAMYYCARVDGYRGYNMDYWGQGTSVTVSS | anti-SSEA4 Heavy chain hMC41 |
| 24 | ENVLTQSPAIMSASPGEKVTMTCSASSSVSYMHWYQQKSNTSPKLWIYDTSKLASGVPGRFSGRGSGNSYSLTISSMEAEDVATYYCFQGSGYPLTFGSGTKLEIKR | anti-SSEA4 Light chain 10G |
| 25 | GFSLKNYGVS | anti-SSEA4(2), anti-SSEA4(3) CDRH 1 |
| 26 | VIWGDGSTNYHSTLRS | anti-SSEA4(2) CDRH2 |
| 27 | PGRGYAMDY | anti-SSEA4(2) CDRH3 |
| 28 | SASSSVSYMH | anti-SSEA4(2), anti-SSEA4(3) CDRL1 |
| 29 | YDTSKLTS | anti-SSEA4(2) anti-SSEA4(3) CDRL2 |
| 30 | FQGSGYPLT | anti-SSEA4(2) anti-SSEA4(3) CDRL3 |
| 31 | VIWGDGSTNYYADSVKG | anti-SSEA4(3) CDRH2 |
| 32 | PGAGYAMDY | anti-SSEA4(3) CDRH3 |
| 33 | QVQLQESGPGLVAPSQTLSITCTVSGFSLKNYGVSWVRQPPGKGLEWIGVIWGDGSTNYHSTLRSRVTISKDNSKQLFLKLNRLQTDDTATYYCAKPGRGYAMDYWGQGTLVTVSS | anti-SSEA4(2) Heavy chain |
| 34 | QIVLTQSPAIMSVYPGEKVTMTCSASSSVSYMHWYQQKSTSPKLWIYDTSKLTSGVPGRFSGSGSGNSYSLTISSMEAEDVATYYCFQGSGYPLTFGGGTKLEIKR | anti-SSEA4(2) Light chain |
| 35 | QVQLVESGGGVVQPGRSLRLSCTVSGFSLKNYGVSWVRQAPGKGLEWVAVIWGDGSTNYYADSVKGRFTISRDNSKNTLYLQMNSLRAEDTAVYYCAKPGAGYAMDYWGQGTSVTVSS | anti-SSEA4(3) Heavy chain |
| 36 | EIVLTQSPATLSLSPGERATLSCSASSSVSYMHWYQQKPGQAPRLLIYDTSKLTSGIPARFSGSGSGTDFTLTISSLEPEDFAVYYCFQGSGYPLTFGQGTKVEIKR | anti-SSEA4(3) Light chain |
| 37 | QVQLQESGPGLVAPSETLSITCTVSGFSLSSQGVYWVRQPPGKGLEWLGAIWAGGSTNYNSALMSRLSISKDNSKLKMNSLTAADTAMYYCARVDGYRGYNMDYWGQGTSVTVSSGGGGSGGGGSGGGGSENVLTQSPAIMSASPGEKVTMTCSASSSVSYMHWYQQKSNTSPKLWIYDTSKLASGVPGRFSGRG | scFv-SSEA4 |

TABLE 1-continued

| SEQ ID NO: | Sequence | Description |
|---|---|---|
|  | SGNSYSLTISSMEAEDVATY YCFQGSGYPLTFGSGTKLEI KR |  |
| 38 | VEPKSCDKTHTCPPCPAPEL LGGPSVFLFPPKPKDTLMIS RTPEVTCVVVDVSHEDPEVK FNWYVDGVEVHNAKTKPREE QYNSTYRVVSVLTVLHQDWL NGKEYKCKVSNKALPAPIEK TISKAKGQPREPQVYTLPPS REEMTKNQVSLTCLVKGFYP SDIAVEWESNGQPENNYKTT PPVLDSDGSFFLYSKLTVDK SRWQQGNVFSCSVMHEALHN HYTQKSLSLSPGK | Fc region |
| 39 | GGGGSGGGGSGGGGS | Linker region |

In one embodiment of the disclosure, the antibody or antigen-binding fragment thereof comprises the CDRH1 region being SEQ ID NO: 13, the CDRH2 region being SEQ ID NO: 8, the CDRH3 region being SEQ ID NO: 9, the CDRL1 region being SEQ ID NO: 10, the CDRL2 region being SEQ ID NO: 20 and the CDRL3 region being SEQ ID NO: 12.

In one embodiment of the disclosure, the antibody or antigen-binding fragment thereof comprises the CDRH1 region being SEQ ID NO: 13, the CDRH2 region SEQ ID NO: 15, the CDRH3 region being SEQ ID NO: 9, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 13, the CDRH2 region being SEQ ID NO: 8, the CDRH3 region being SEQ ID NO: 16, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 14, the CDRH2 region being SEQ ID NO: 8, the CDRH3 region being SEQ ID NO: 17, the CDRL1 region being SEQ ID NO: 10, the CDRL2 region being SEQ ID NO: 21 and the CDRL3 region being SEQ ID NO: 12.

In one embodiment of the disclosure, the antibody or antigen-binding fragment thereof comprises the CDRH1 region being SEQ ID NO: 14, the CDRH2 region being SEQ ID NO: 8, the CDRH3 region being SEQ ID NO: 18, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 15, the CDRH3 region being SEQ ID NO: 9, the CDRL1 region being SEQ ID NO: 10, the CDRL2 region being SEQ ID NO: 20 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 15, the CDRH3 region being SEQ ID NO: 17, the CDRL1 region being SEQ ID NO: 10, the CDRL2 region being SEQ ID NO: 11 and the CDRL3 region being SEQ ID NO: 12.

In one embodiment of the disclosure, the antibody or antigen-binding fragment thereof comprises the CDRH1 region being SEQ ID NO: 7, the CDRH2 region being SEQ ID NO: 8, the CDRH3 region being SEQ ID NO: 16, the CDRL1 region being SEQ ID NO: 10, the CDRL2 region being SEQ ID NO: 20 and the CDRL3 region being SEQ ID NO: 12.

In one embodiment of the disclosure, the CDRs of a heavy chain and a light chain are listed in Table 2.

TABLE 2

| combination | CDR1 (SEQ ID NO) | CDR2 (SEQ ID NO) | CDR3 (SEQ ID NO) |
|---|---|---|---|
| Heavy chain | SIGVY (13) | AIWAGGST NYNSALMS (8) | VDGYRGYNMDY (9) FQGSGYPL (12) |
| Light chain | SSVSY (10) | DHS (20) |  |
| Heavy chain | SIGVY (13) | AGWAGGST NYNSALMS (15) | VDGYRGYNMDY (9) FQGSGYPL (12) |
| Light chain | SSVSY (10) | DTS (11) |  |
| Heavy chain | SIGVY (13) | AIWAGGST NYNSALMS (8) | IDGYRGYNMDY (16) FQGSGYPL (12) |
| Light chain | SSVSY (10) | DTS (11) |  |
| Heavy chain | STGVY (14) | AIWAGGST NYNSALMS (8) | VDGYRGYGMDY (17) FQGSGYPL (12) |
| Light chain | SSVSY (10) | DVS (21) |  |
| Heavy chain | STGVY (14) | AIWAGGST NYNSALMS (8) | VDGYRGYQMDY (18) FQGSGYPL (12) |
| Light chain | SSVSY (10) | DTS (11) |  |
| Heavy chain | SQGVY (7) | AGWAGGST NYNSALMS (15) | VDGYRGYNMDY (9) FQGSGYPL (12) |
| Light chain | SSVSY (10) | DHS (20) |  |
| Heavy chain | SQGVY (7) | AGWAGGST NYNSALMS (15) | VDGYRGYGMDY (17) FQGSGYPL (12) |
| Light chain | SSVSY (10) | DTS (11) |  |
| Heavy chain | SQGVY (7) | AIWAGGST NYNSALMS (8) | IDGYRGYNMDY (16) FQGSGYPL (12) |
| Light chain | SSVSY (10) | DHS (20) |  |

Bolded and under-lined letters indicate mutagenesis sites.

All the antibodies disclosed in the present disclosure have a significant improvement in affinity to SSEA4 compared to a wild-type antibody.

In one embodiment of the disclosure, the antibody or antigen-binding fragment thereof comprises a heavy chain variable region comprising the amino acid sequence of

SEQ ID NO: 23
(QVQLQESGPGLVAPSETLSITCTVSGFSLSSQGVYWVRQPP

GKGLEWLGAIWAGGSTNYNSALMSRLSISKDNSKSQVFLKMN

SLTAADTAMYYCARVDGYRGYNMDYWGQGTSVTVSS)

or a substantially similar sequence thereof and a light chain variable region comprising the amino acid sequence of SEQ ID NO: 24
(ENVLTQSPAIMSASPGEKVTMTCSAS<u>SSVS</u>YMHWYQQKSNTSP KLWIY<u>DTS</u>KLASGVPGRFSGRGSGNSYSLTISSMEAEDVATYYC <u>FQGSGYPLT</u>FGSGTKLEIKR)

or a substantially similar sequence thereof. The under-lined letters indicate CDR regions. Preferably, the antibody or antigen-binding fragment thereof comprises a heavy chain variable region comprising the amino acid sequence of SEQ ID NO: 23 or a substantially similar sequence thereof having at least 90%, at least 95%, at least 98% or at least 99% sequence identity. Preferably, the antibody or antigen-binding fragment thereof comprises a light chain variable region comprising the amino acid sequence of SEQ ID NO: 24 or a substantially similar sequence thereof having at least 90%, at least 95%, at least 98% or at least 99% sequence identity.

In one embodiment of the disclosure, the antibody or antigen-binding fragment thereof is a single-chain FAT (scFv) molecule comprising the amino acid sequence of SEQ ID NO: 37.

In one embodiment of the disclosure, the antigen-binding fragment is fused to an Fc region having the amino acid sequence of SEQ ID NO: 38.

The antibody according to the disclosure can be full-length (for example, an IgG1 or IgG4 antibody) or may comprise only an antigen-binding portion (for example, an Fab, F(ab')$_2$ or scFv fragment), and may be modified to affect functionality as needed.

The antibody or antigen-binding fragment thereof according to the disclosure specifically binds to SSEA4. SSEA4 is a hexasaccharide belonged to globo-series glycosphingolipids (GSLs) and comprises the structure of Neu5Acα2→3 Galβ1→3 GalNAcβ1→3 Galα1→4Galβ1→4Glcβ1. SSEA4 is overexpressed in many epithelial cancers, including ovarian, gastric, prostate, lung, breast, and pancreatic cancers, as well as in renal cell carcinoma and glioblastoma multiforme.

The antibody described herein also includes an antigen-binding fragment of a full antibody molecule. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment includes: (i) Fab fragments; (ii) to F(ab')$_2$ fragments; (iii) Fd fragments; (iv) Fv fragments; (v) single-chain Fv molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment may fuse to at least one constant domain, such as an Fc region, namely an Fc-fused antigen-binding fragment. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In some embodiments of the disclosure, the antigen-binding fragment is $V_H$-$V_L$, and the Fc-fused antigen-binding fragment is $V_H$-$V_L$-Fc. In any configuration of variable and constant domains, including any of the exemplary configurations listed above, the variable and constant domains, the adjacent variable domains, or the adjacent constant domains may be either directly linked to one another or may be linked by a full or partial hinge or linker region. In some embodiments of the disclosure, the antigen-binding fragment is $V_H$-linker-$V_L$, and the Fc-fused antigen-binding fragment is $V_H$-linker-$V_L$-Fc. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments of the disclosure, the linker region is three copies of G4S (SEQ ID NO: 39). Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

Preferably, the antibody or antigen-binding fragment thereof according to the disclosure is a mammalian antibody. The term "mammalian antibody", as used herein, is intended to include antibodies having variable and constant regions derived from mammalian germline immunoglobulin sequences. The mammalian antibodies of the disclosure may include amino acid residues not encoded by mammalian germline immunoglobulin sequences (e.g., mutations introduced by random or site-specific mutagenesis in vitro or by somatic mutation in vivo), for example in the CDRs and in particular CDR3.

Mammalian antibodies such as human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The anti-SSEA4 antibody disclosed herein comprises one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes an anti-SSEA4 antibody comprising variants of any of the $V_H$, $V_L$, and/or CDR amino acid sequences disclosed herein having one or more conservative substitutions. For example, the present disclosure includes an anti-SSEA4 antibody having $V_H$, $V_L$, and/or CDR amino acid sequences with, e.g., 6 or fewer, 5 or fewer, 4 or fewer, 3 or fewer, etc. conservative amino acid substitutions relative to any of the $V_H$, $V_L$, and/or CDR amino acid sequences disclosed herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, to alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Preferably, the antibody according to the disclosure is a monoclonal antibody.

The antibodies of the present disclosure may be monospecific, bi-specific, or multispecific. Multispecific antibodies may be specific for different epitopes of one target polypeptide or may contain antigen-binding domains specific for more than one target polypeptide. The anti-SSEA4 antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for SSEA4 or a fragment thereof, and the other arm of the immunoglobulin is specific for a second therapeutic target or is conjugated to a therapeutic moiety.

In one embodiment of the disclosure, the antibody or antigen-binding fragment thereof can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3. sup.rd ed. 1997)).

Techniques for the production of single chain antibodies or recombinant antibodies (U.S. Pat. Nos. 4,946,778, 4,816, 567) can be adapted to produce antibodies to polypeptides of this disclosure. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

Preferably, the antibody or antigen-binding fragment thereof according to the present disclosure is a glycoantibody. The term "glycoantibody" as used herein refers to a homogeneous population of monoclonal antibodies having a single, uniform glycoform on Fc region. The individual glycoantibodies in the homogeneous population are identical, bind to the same epitope, and contain the same Fc glycan with a well-defined glycan structure and sequence.

The term "homogeneous" in the context of a glycosylation profile of Fc region is used interchangeably and are intended to mean a single glycosylation pattern represented by one desired N-glycan species, with little or no trace amount of precursor N-glycan. In certain embodiments, the trace amount of the precursor N-glycan is less than about 2%.

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is an Asn-X-Ser or Asn-X-Thr sequence, where X is any amino acid except praline.

As used herein, the term "N-glycan" refers to an N-linked oligosaccharide attached by an N-acetylglucosamine (GlcNAc) linked to the amide nitrogen of an asparagine residue in an Fc-containing polypeptide.

In one preferred embodiment of the disclosure, the antibody or antigen-binding fragment thereof has a glycol-engineered N-glycan. The antibody comprises an Fc region or the antigen-binding fragment is fused to an Fc region, and the antibody or antigen-binding fragment thereof has an N-glycan on the Fc region, and the N-glycan is selected from the group consisting of Man$_5$GlcNAc$_2$ (Man5), GlcNAc$_2$Man$_3$GlcNAc$_2$(Fuc) (G0F), GalGlcNAc$_2$Man$_3$GlcNAc$_2$(Fuc) (G1F), Gal$_2$GlcNAc$_2$Man$_3$GlcNAc$_2$(Fuc) (G2F), Sia$_2$(α2-3)Gal$_2$GlcNAc$_2$Man$_3$GlcNAc$_2$(Fuc) (G2S2F (alpha 2,3 linkage)), Sia$_2$(α2-6)Gal$_2$GlcNAc$_2$Man$_3$GlcNAc$_2$(Fuc) (G2S2F (alpha 2,6 linkage)), GlcNAc$_2$Man$_3$GlcNAc$_2$ (G0), Gal$_2$GlcNAc$_2$Man$_3$GlcNAc$_2$ (G2), Sia$_2$(α2-3)Gal$_2$GlcNAc$_2$Man$_3$GlcNAc$_2$ (G2S2 (alpha 2,3 linkage)), and Sia$_2$(α2-6)Gal$_2$GlcNAc$_2$Man$_3$GlcNAc$_2$ (G2S2 (alpha 2,6 linkage)).

In one preferred embodiment of the disclosure, the antibody comprises a heavy chain variable region comprising the amino acid sequence of SEQ ID NO: 23 and a light chain variable region comprising the amino acid sequence of SEQ ID NO: 24, and the N-glycan is selected from the group consisting of Man5, G0F, G1F and G2F. Specifically, a plurality of the antibodies or antigen-binding fragment thereof are provided in a population.

The schematic structures of the N-glycan are shown in FIG. 1.

In another aspect, the antibody or antigen-binding fragment thereof according to the disclosure has a defucosylated glycoform. As used herein, the term "defucosylated" refers to the absence of a core fucose in the N-glycan of an Fc region. Preferably, the engineered N-glycan is selected from the group consisting of G0, G2, G2S2 (alpha 2,3 linkage), and G2S2 (alpha 2,6 linkage).

In another aspect, the antibody or antigen-binding fragment thereof according to the disclosure has a glycoengineered Fc. As used herein, the term "glycoengineered Fc" when used herein refers to N-glycan on the Fc region has been altered or engineered either enzymatically or chemically. The term "Fc glycoengineering" as used herein refers to the enzymatic or chemical process used to make the glycoengineered Fc. Exemplary methods of engineering are described in, for example, Wong et al U.S. Ser. No. 12/959,351, the contents of which is hereby incorporated by reference. Preferably, the engineered N-glycan is selected from the group consisting of G0F, G2F, G2S2F (alpha 2,3 linkage), G2S2F (alpha 2,6 linkage), G0, G2, G2S2 (alpha 2,3 linkage), and G2S2 (alpha 2,6 linkage), and a plurality of the antibodies or antigen-binding fragment thereof are provided in a population, and more than about 90% of the population has the same N-glycan.

The schematic structures of the engineered N-glycan are shown in Table 4.

TABLE 4

| Glycoforms | Percentage (%) |
|---|---|
| G0F | >90% |
| G2F | >90% |
| G2S2F (alpha 2,3 linkage) | >90% |
| G2S2F (alpha 2,6 linkage) | >90% |
| G0 | >90% |
| G2 | >90% |
| G2S2 (alpha2,3 linkage) | >90% |
| G2S2 (alpha2,6 linkage) | >90% |

In some embodiments, a plurality of the antibodies or antigen-binding fragment thereof are provided in a population, and more than about 90% of the population of the antibody or antigen-binding fragment thereof has the same N-glycan.

In another aspect, the present disclosure provides a method for enrichment of cells comprising:
  contacting a pool of cells with an antibody or an antigen-binding fragment thereof, wherein the antibody comprises an Fc region or the antigen-binding fragment is fused to an Fc region to form an Fc-fused antigen-binding fragment, and the antibody or Fc-fused antigen-binding fragment thereof is glycoengineered on the Fc region; and
  isolating cells binding to the antibody or Fc-fused antigen-binding fragment thereof from the pool.

In another aspect, the present disclosure also provides a method for enrichment of cells comprising:
  contacting a pool of cells with an antibody or antigen-binding fragment thereof, wherein the antibody comprises an Fc region, or the antigen-binding fragment is fused to an Fc region to form an Fc-fused antigen-binding fragment, and the antibody or Fc-fused antigen-binding fragment thereof is glycoengineered on the Fc region; and
  isolating cells binding to the antibody or Fc-fused antigen-binding fragment thereof from the pool.

The present disclosure also provides a kit for enrichment of cells comprising an antibody or antigen-binding fragment thereof, wherein the antibody comprises an Fc region or the antigen-binding fragment is fused to an Fc region, and the antibody or antigen-binding fragment thereof is glycoengineered on the Fc region; and a support for immobilizing the antibody or antigen-binding fragment thereof.

In one aspect, the present disclosure provides a kit for enrichment of cells comprising an antibody or antigen-binding fragment thereof, wherein the antibody comprises an Fc region, or the antigen-binding fragment is fused to an Fc region to form an Fc-fused antigen-binding fragment, and the antibody or Fc-fused antigen-binding fragment thereof is glycoengineered on the Fc region, and a support for immobilizing the antibody or antigen-binding fragment thereof.

In another embodiment of the disclosure, the kit further comprises an antigen. The antigen can link to the support. In some embodiments of the disclosure, the antigen binds to the antibody or antigen-binding fragment thereof. Preferably, the antigen is SSEA4.

In one embodiment of the disclosure, the antibody or antigen-binding fragment is an anti-SSEA4 antibody or SSEA4-binding fragment.

The immune cells according to the disclosure are antibody-binding cells. In one embodiment of the disclosure, the immune cells bind to an Fab region of the antibody or antigen-binding fragment thereof. In one another embodiment of the disclosure, the immune cells bind to an Fc region of the antibody or Fc-fused antigen-binding fragment thereof. In some embodiments of the disclosure, the immune cells are selected from the group consisting of natural killer cells, natural killer T cells, macrophages, monocytes and B cells.

As used herein, the term "enrichment" refers to a process of increasing a proportion of the immune cells in a sample. Preferably, the enrichment is a process of partial purification or a partial selection.

As used herein, the term "a pool of cells" refers to a group of cells containing the immune cells. Normally, the pool of cells according to the disclosure comprises other cells. Preferably, the pool of cells is a sample derived from a subject. As used herein, the term "sample" encompasses a variety of sample types obtained from an individual, subject or patient. The definition encompasses blood and other liquid samples of biological origin, solid tissue samples such as a biopsy specimen or tissue cultures or cells derived therefrom and the progeny thereof. As interchangeably used herein, the terms "individual," "subject," and "patient," refer to a mammal, including, but not limited to, murines (rats, mice), non-human primates, humans, canines, felines, ungulates (e.g., equines, bovines, ovines, porcines, caprines), etc. In one preferred embodiment of the disclosure, the pool of cells is peripheral blood mononuclear cells. More preferably, the peripheral blood mononuclear cells are selected from the group consisting of natural killer cells, natural killer T cells, macrophages, monocytes and B cells When the method according to the disclosure is applied for the enrichment of the immune cells binding to an Fc region of the antibody or Fc-fused antigen-binding fragment thereof and an Fab region or the antigen-binding fragment is immobilized on a support.

Figure 2:
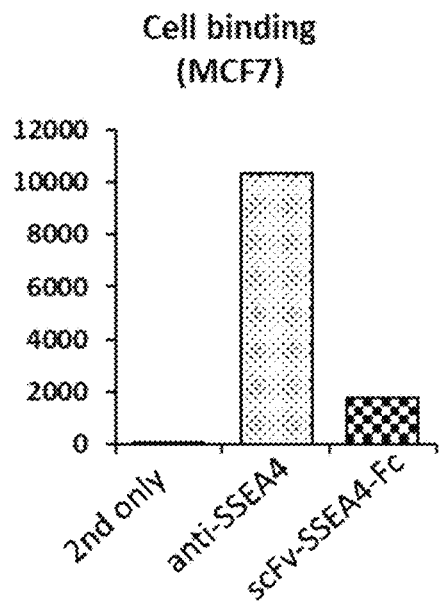
FIG. 2 shows the result of MCF7 cell binding of scFv-SSEA4-Fc fusion.
Figure 3:
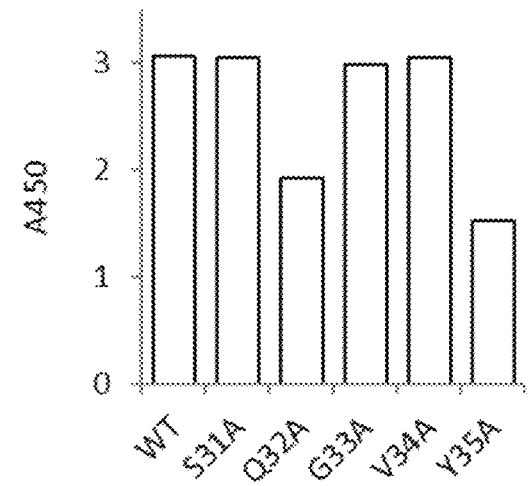
FIGS. 3 (A) to 3 (F) show alanine scanning of α-SSEA-4 variable regions. Ability of antigen binding was assessed by ELISA.
Figure 3:
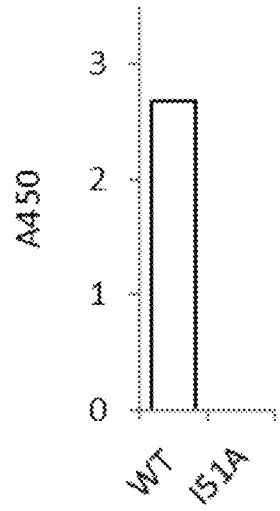
Figure 3:
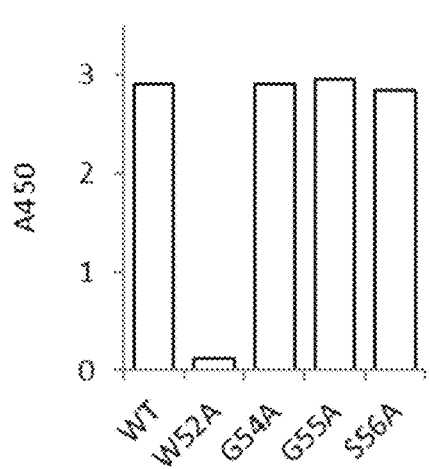
Figure 3:
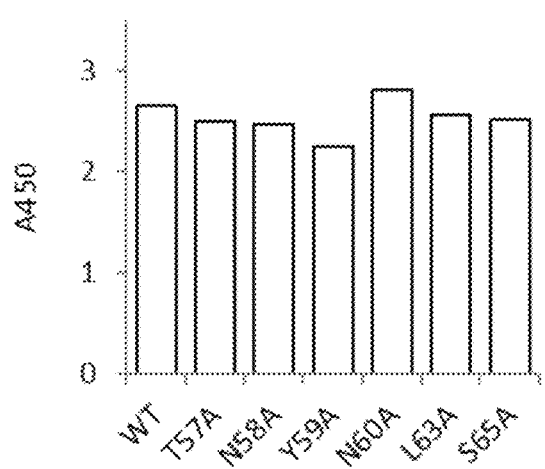
Figure 3:
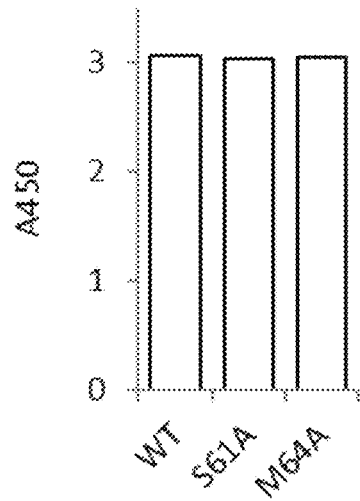
Figure 3:
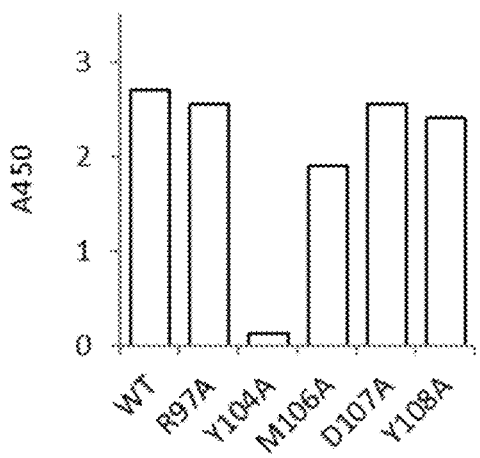
Figure 3:
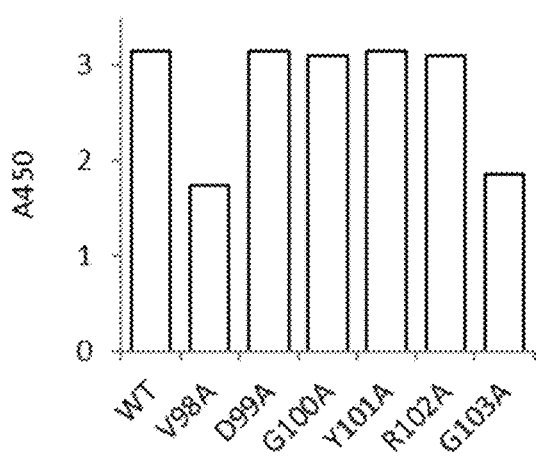
Figure 3:
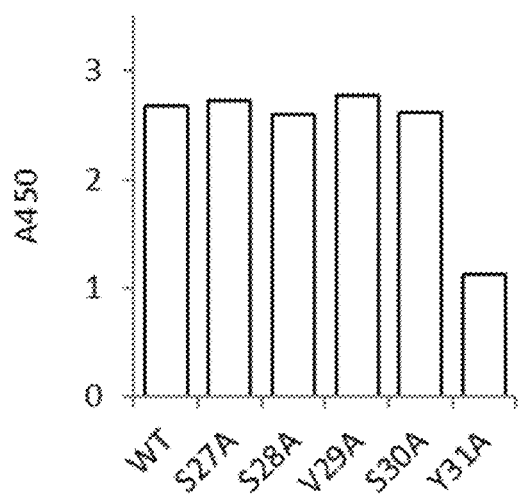
Figure 3:
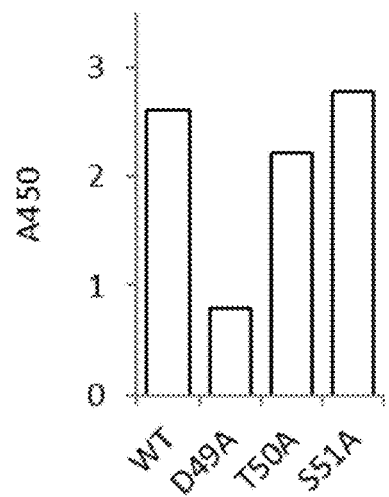
Figure 3:
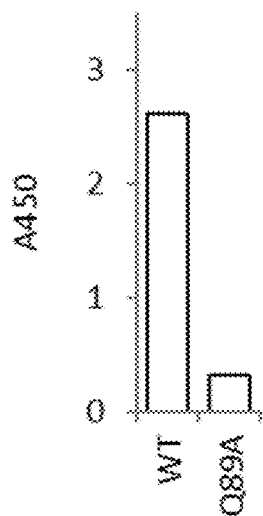
Figure 3:
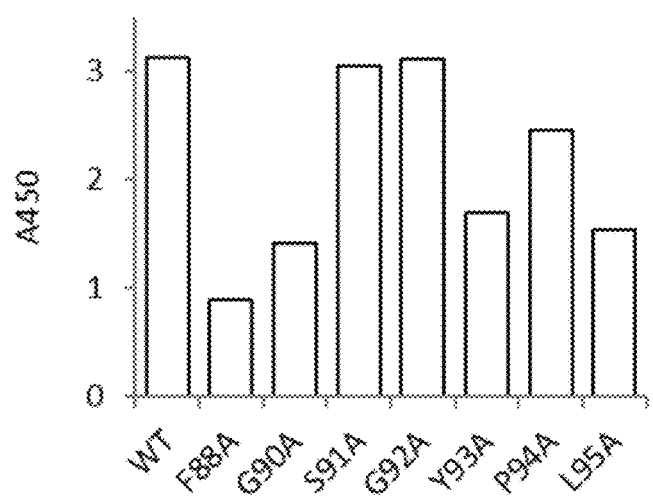
Figure 4:
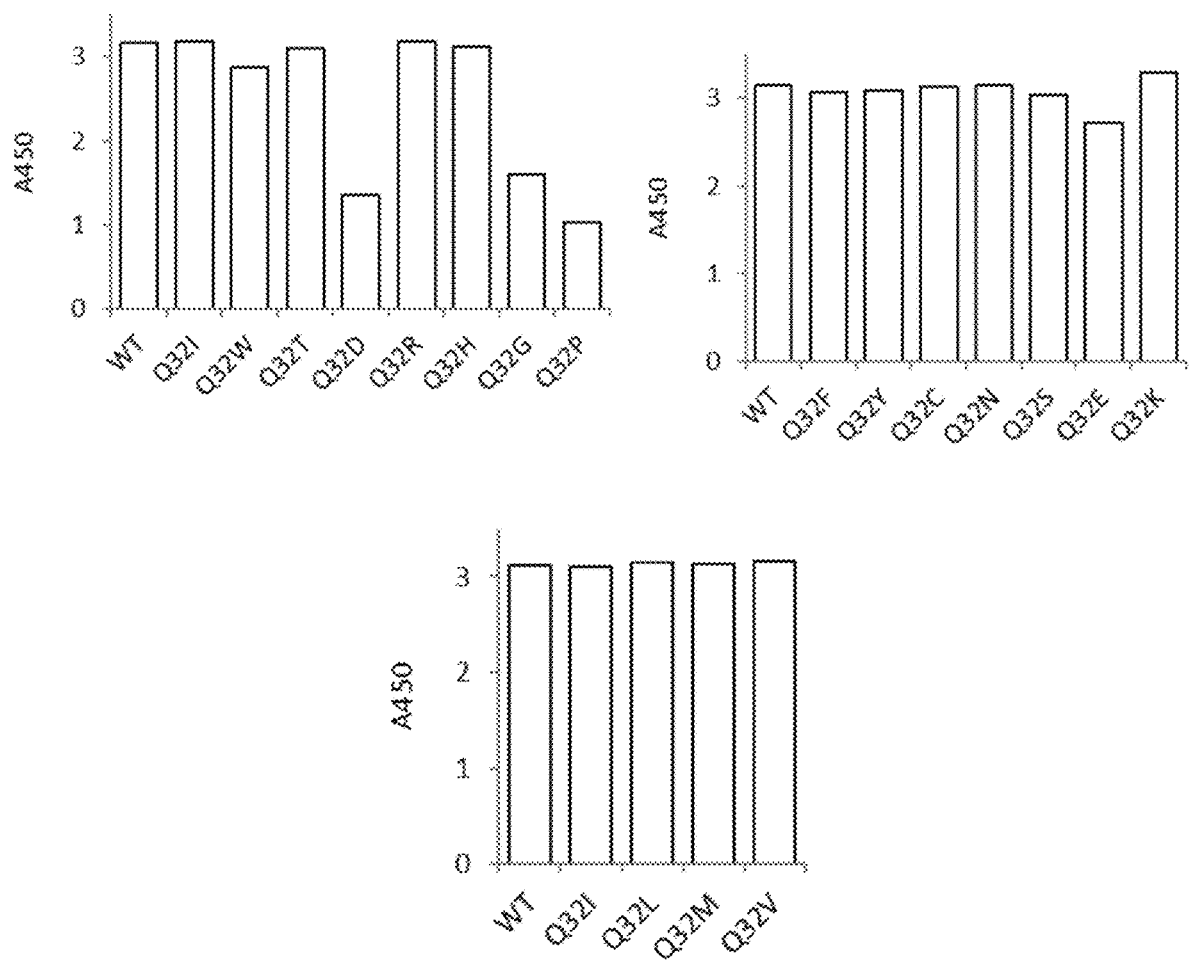
FIGS. 4 (A) to 4 (F) show site-directed mutagenesis of α-SSEA4 heavy chain variable regions. Ability of antigen binding was assessed by ELISA.
Figure 4:
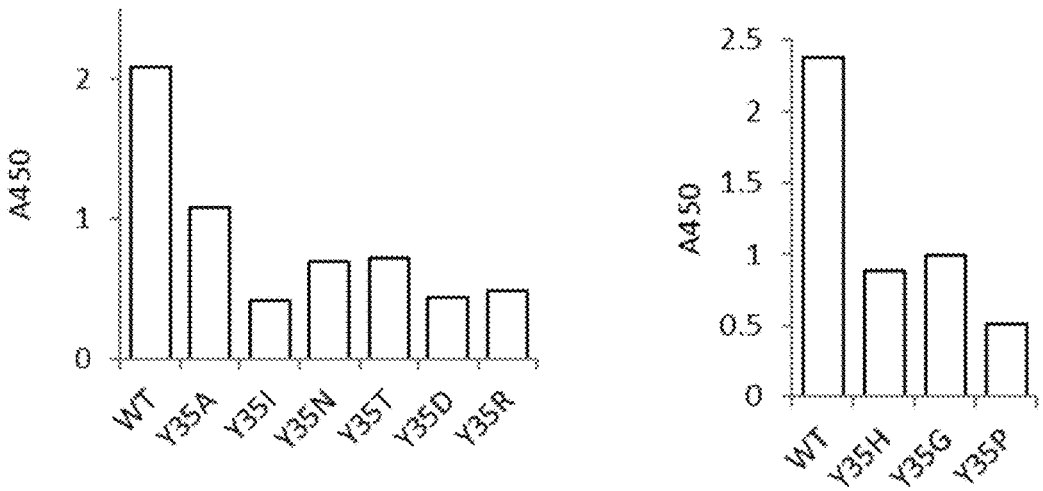
Figure 4:
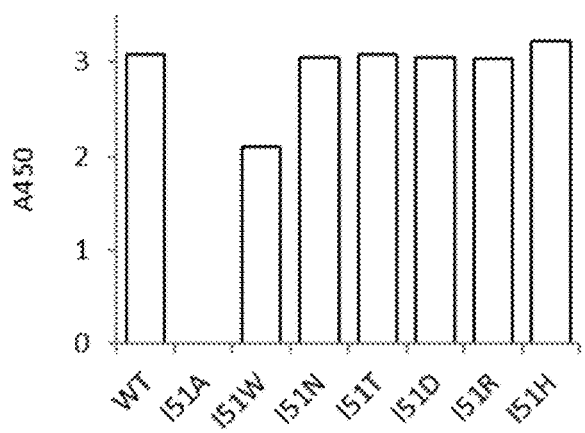
Figure 4:
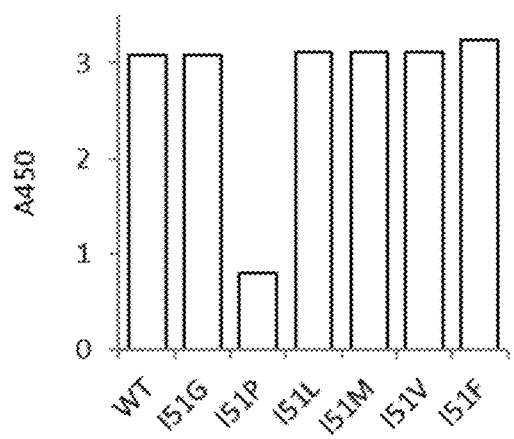
Figure 4:
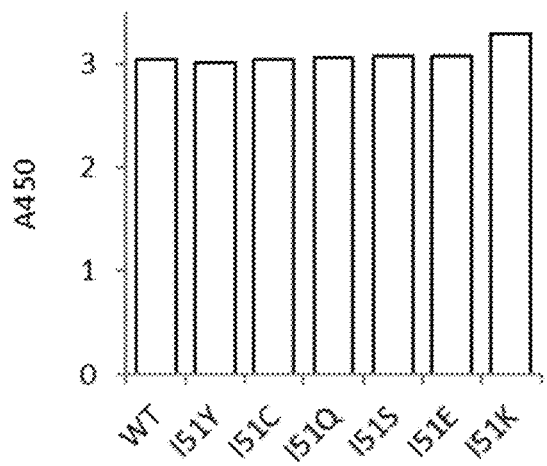
Figure 4:
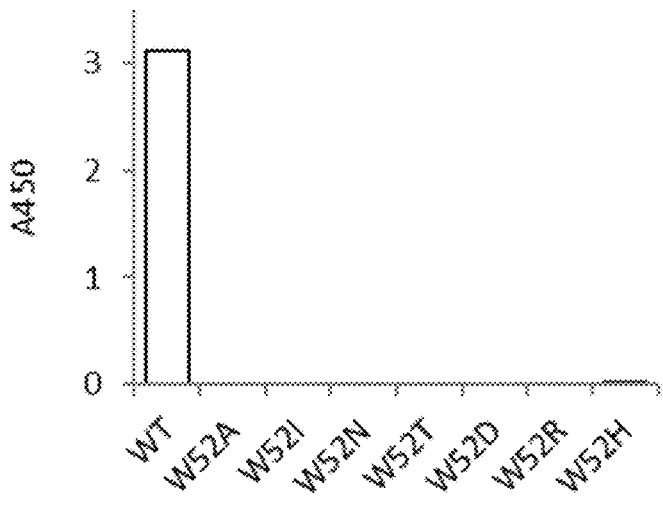
Figure 4:
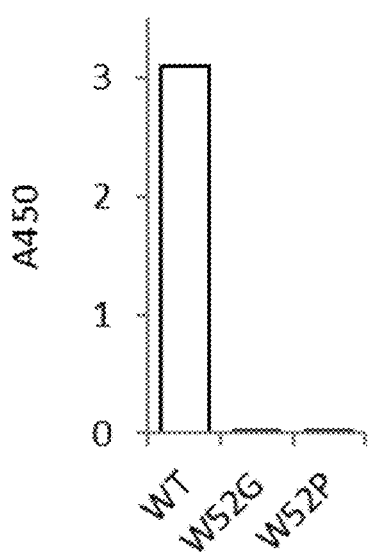
Figure 4:
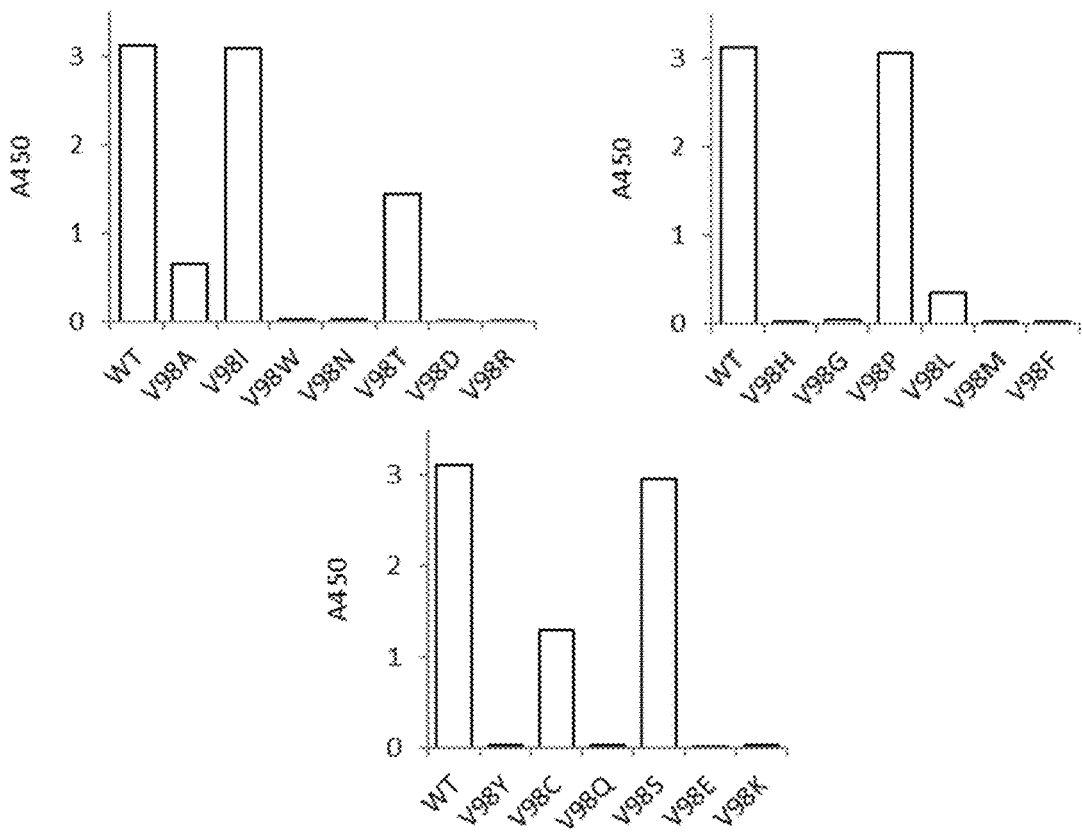
Figure 4:
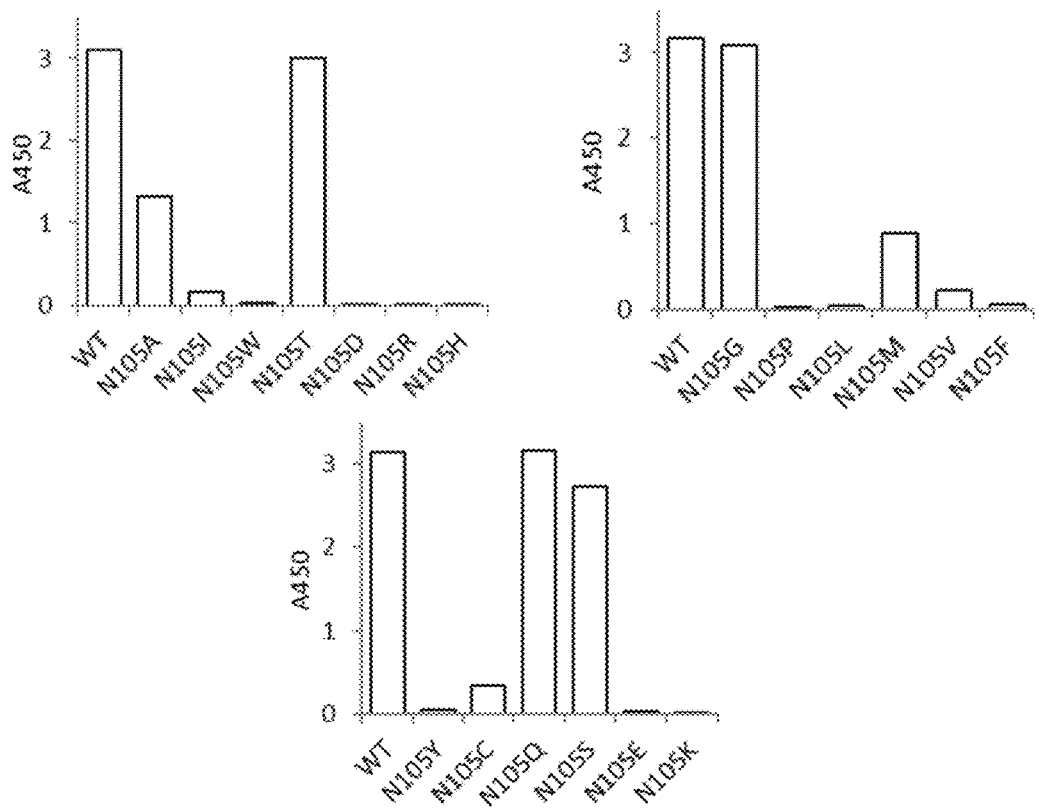
Figure 5:
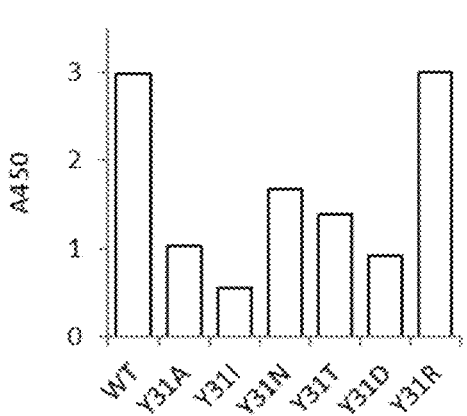
FIGS. 5 (A) to 5 (I) show site-directed mutagenesis of α-SSEA4 light chain variable regions. Ability of antigen binding was assessed by ELISA.
Figure 5:
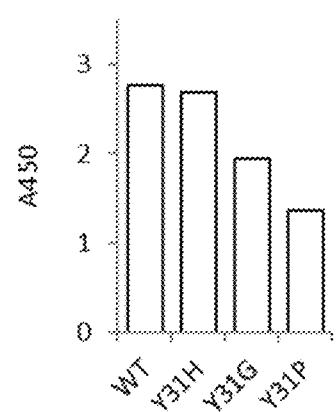
Figure 5:
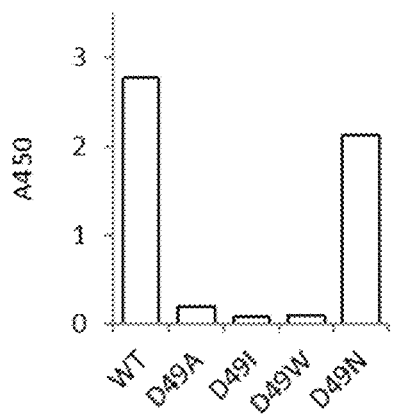
Figure 5:
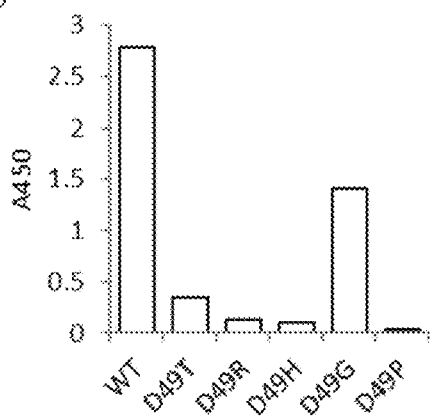
Figure 5:
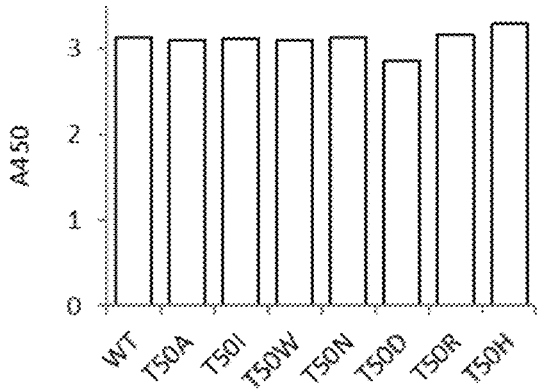
Figure 5:
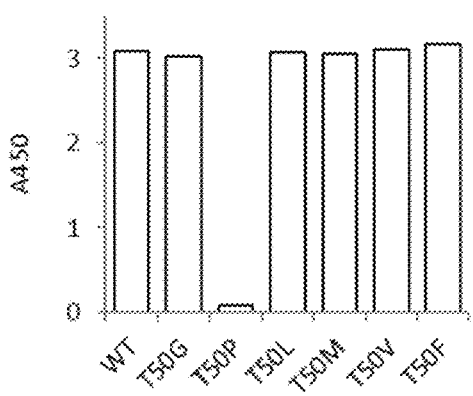
Figure 5:
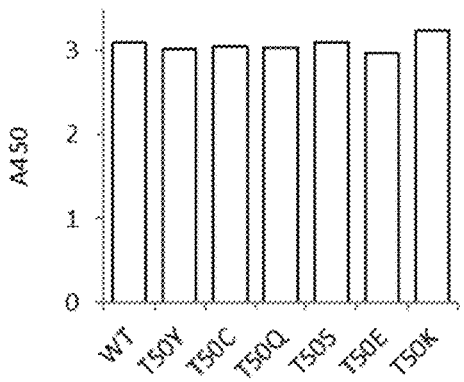
Figure 5:
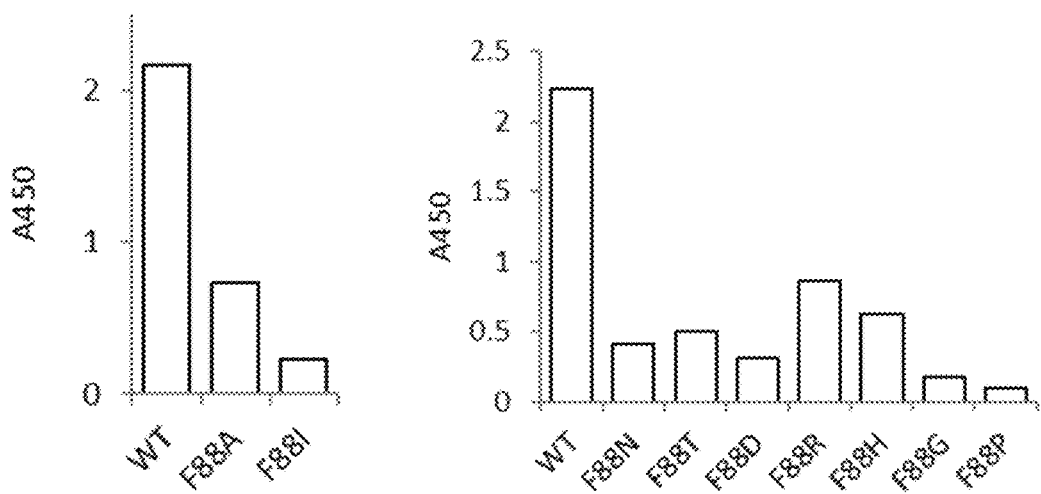
Figure 5:
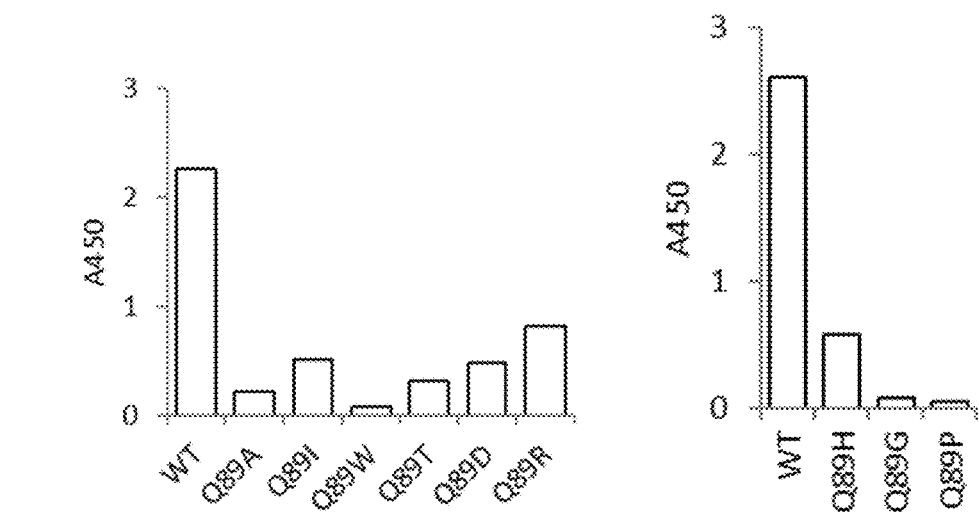
Figure 5:
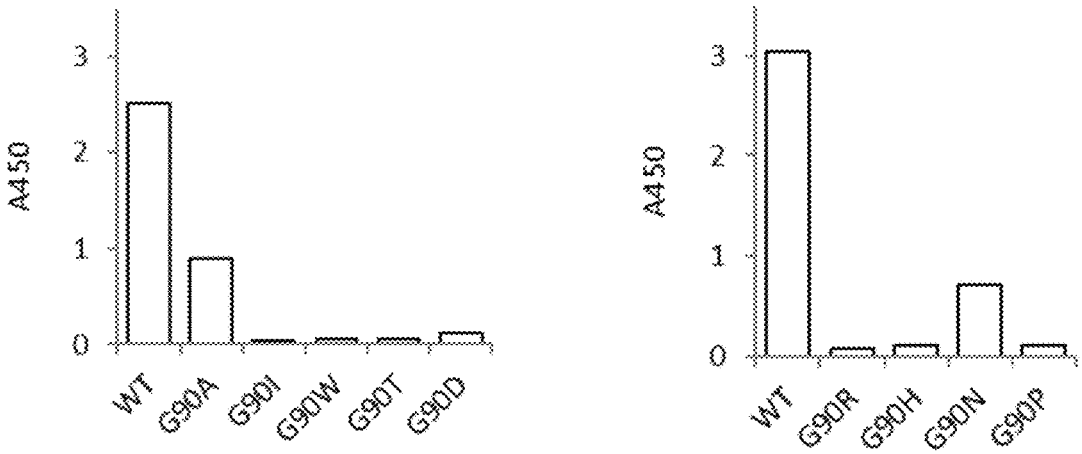
Figure 5:
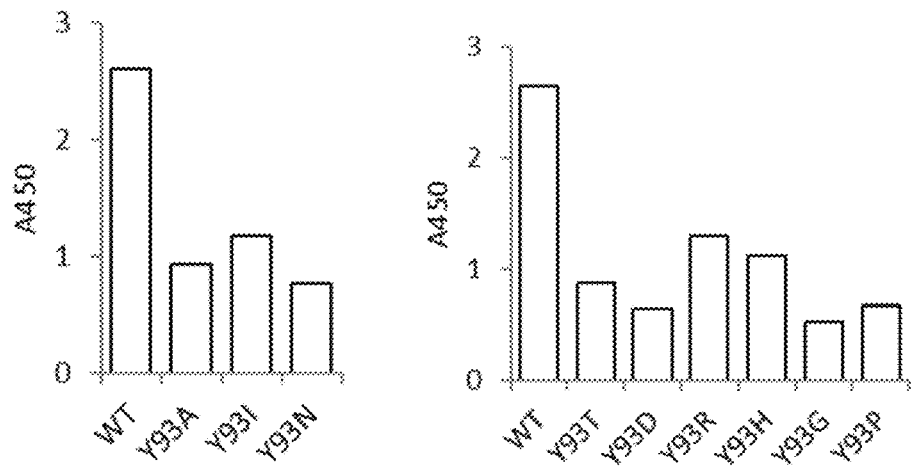
Figure 5:
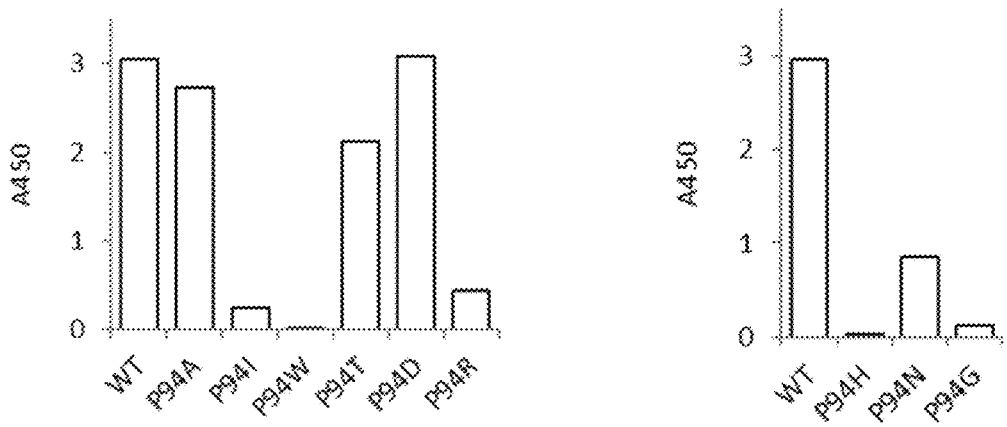
Figure 5:
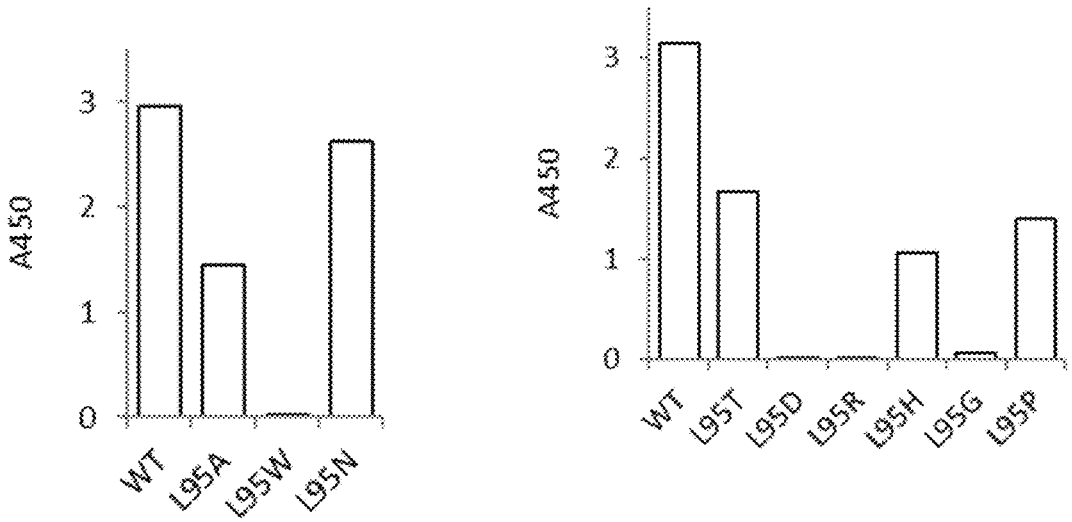
Figure 6:
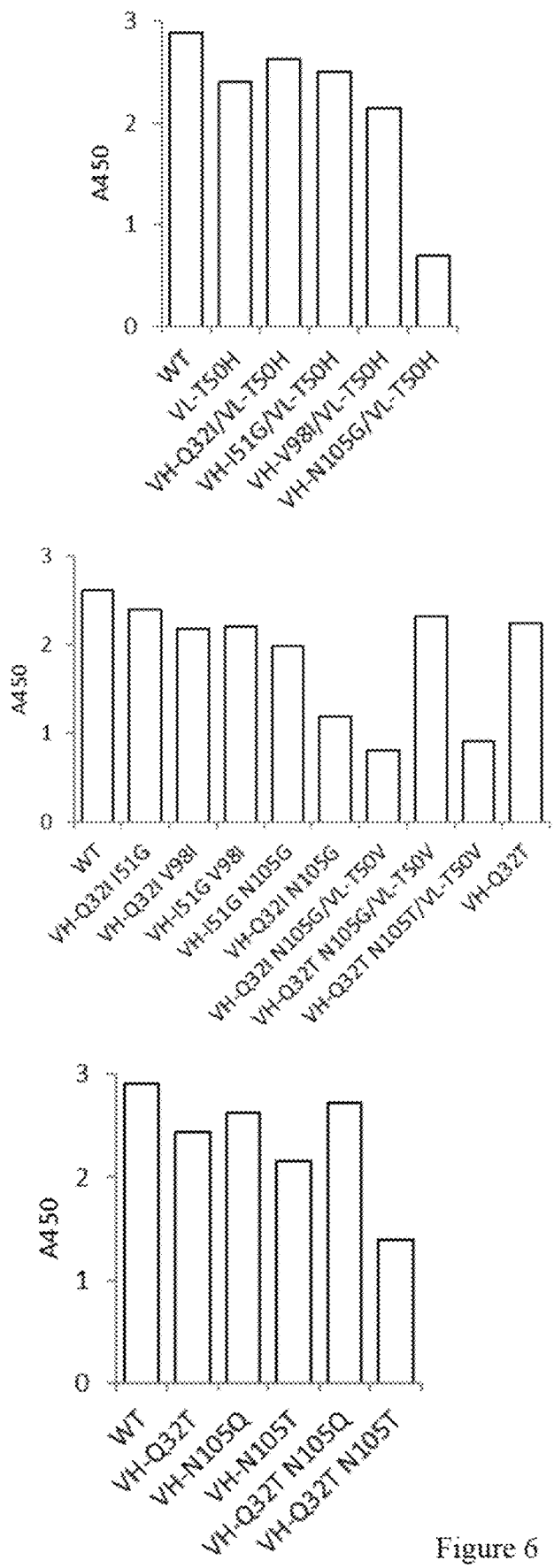
FIG. 6 shows combination of α-SSEA4 heavy chain and light chain mutations (as summarized in Table 2). Ability of antigen binding was assessed by ELISA.
Figure 7:
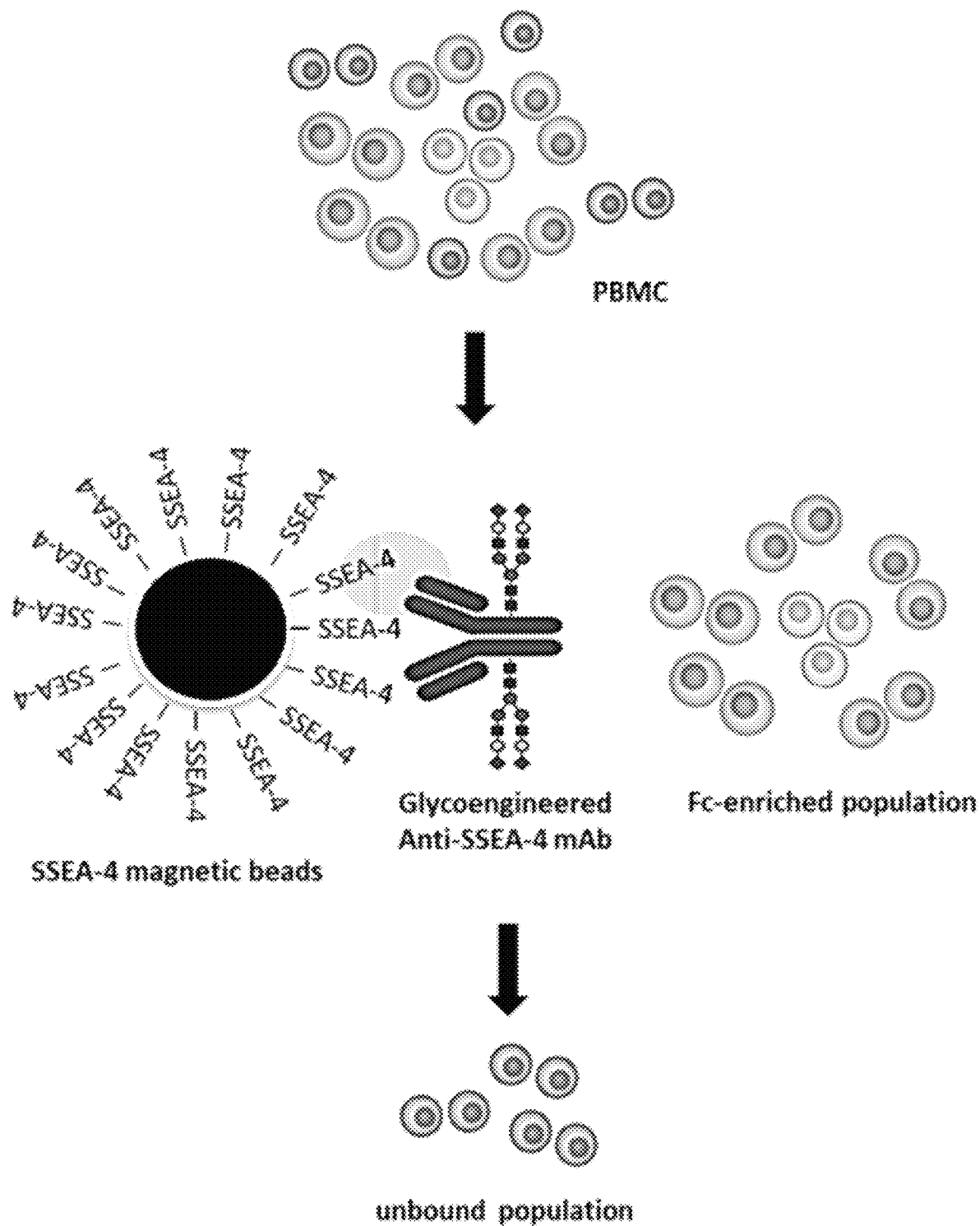
FIG. 7 shows the schematic diagram of one embodiment of the method for the enrichment of the immune cells binding to an Fc region.
Figure 8:
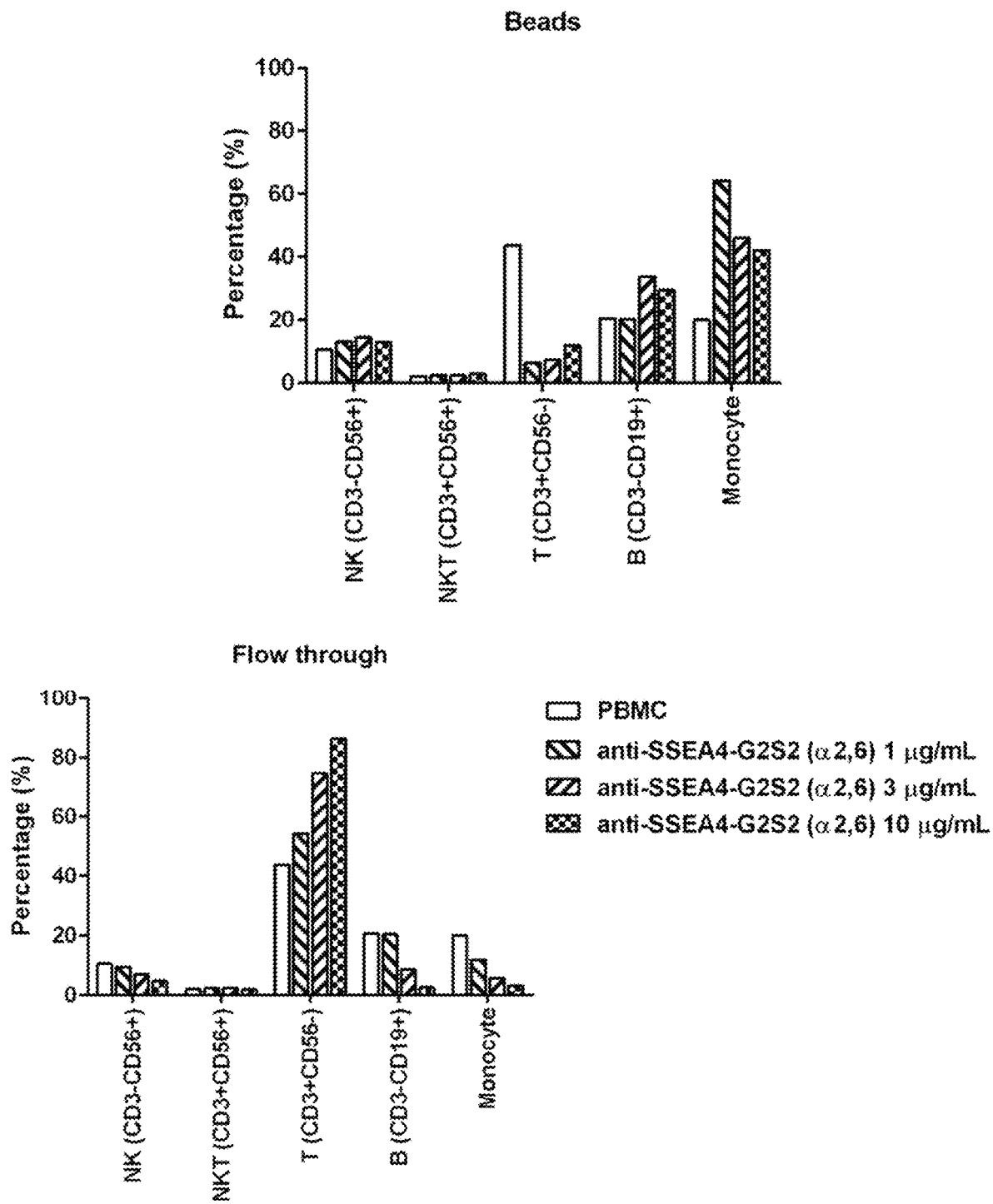
FIG. 8 shows the profiles of immune cells in beads-captured and flow through fractions.
Figure 9:
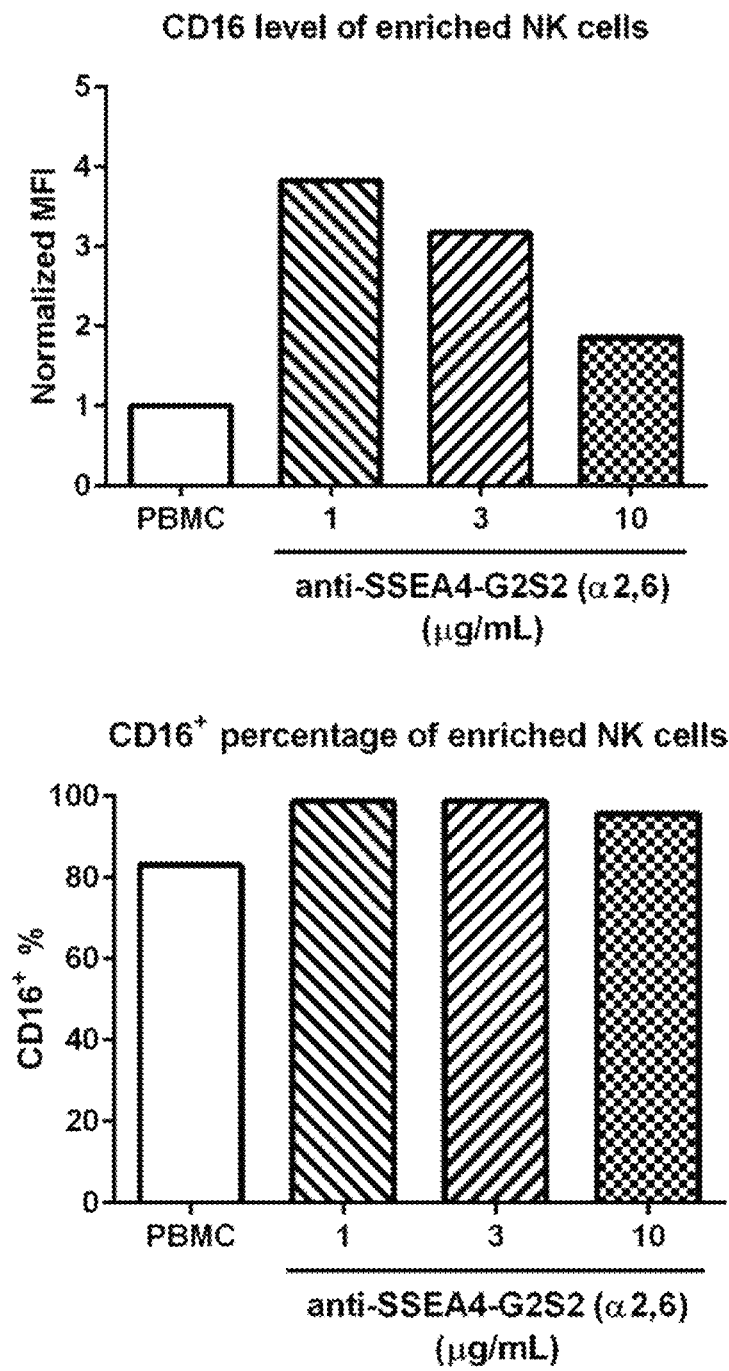
FIG. 9 shows the CD16 expression levels and $CD16^+$ percentages of NK cells in the captured fraction.
Figure 10:
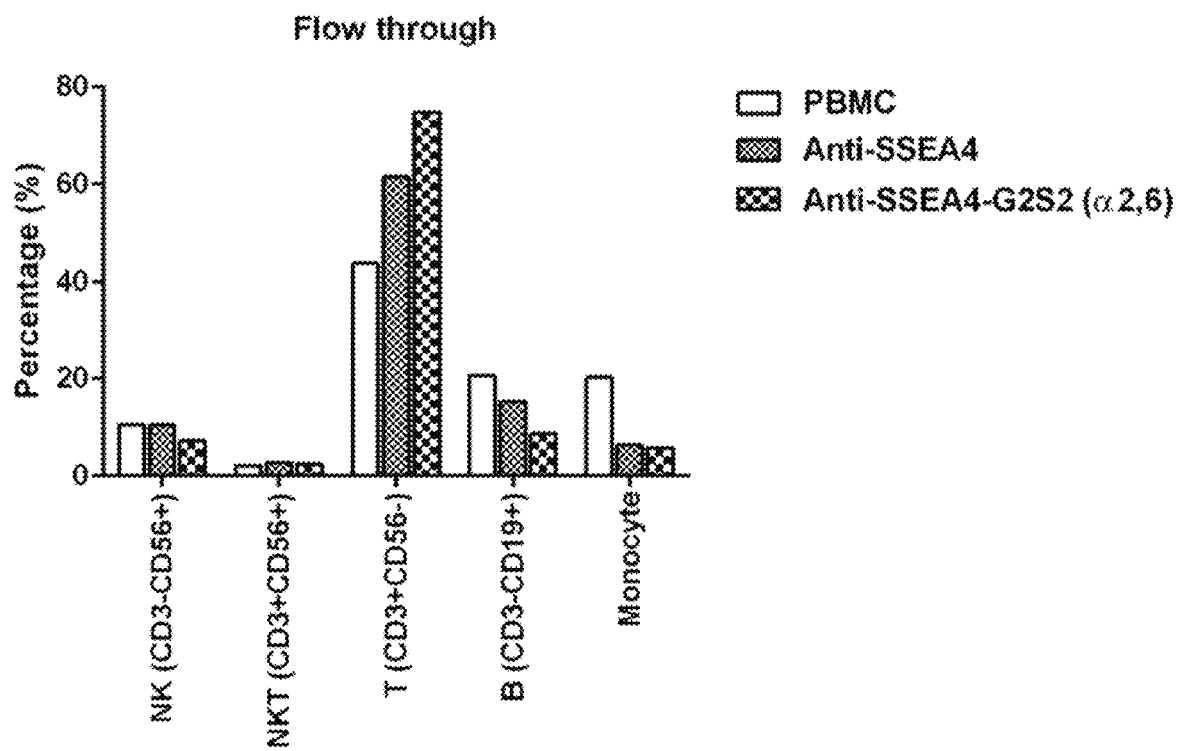
FIG. 10 shows the comparison of flow through fraction of immune cells enrichment using parental or glycoengineered antibodies.
Figure 11:
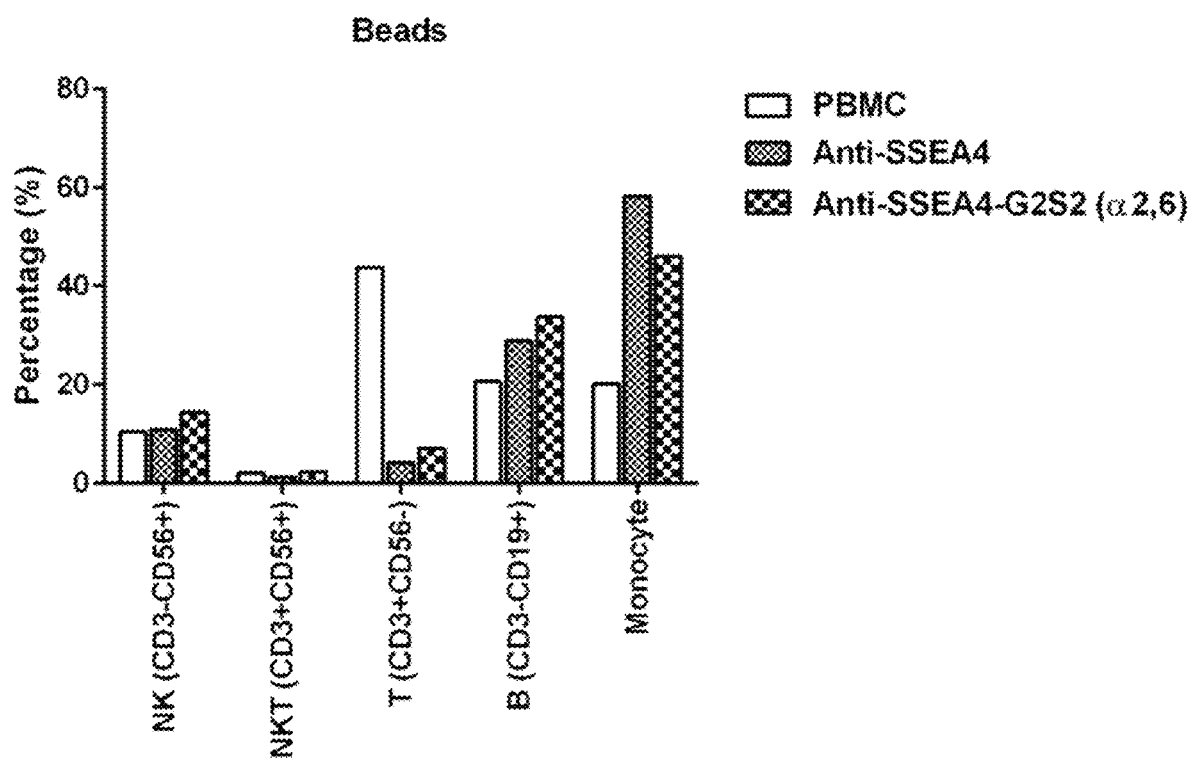
FIG. 11 shows the comparison of beads-captured fraction of immune cells enrichment using parental or glycoengineered antibodies.
Figure 12:
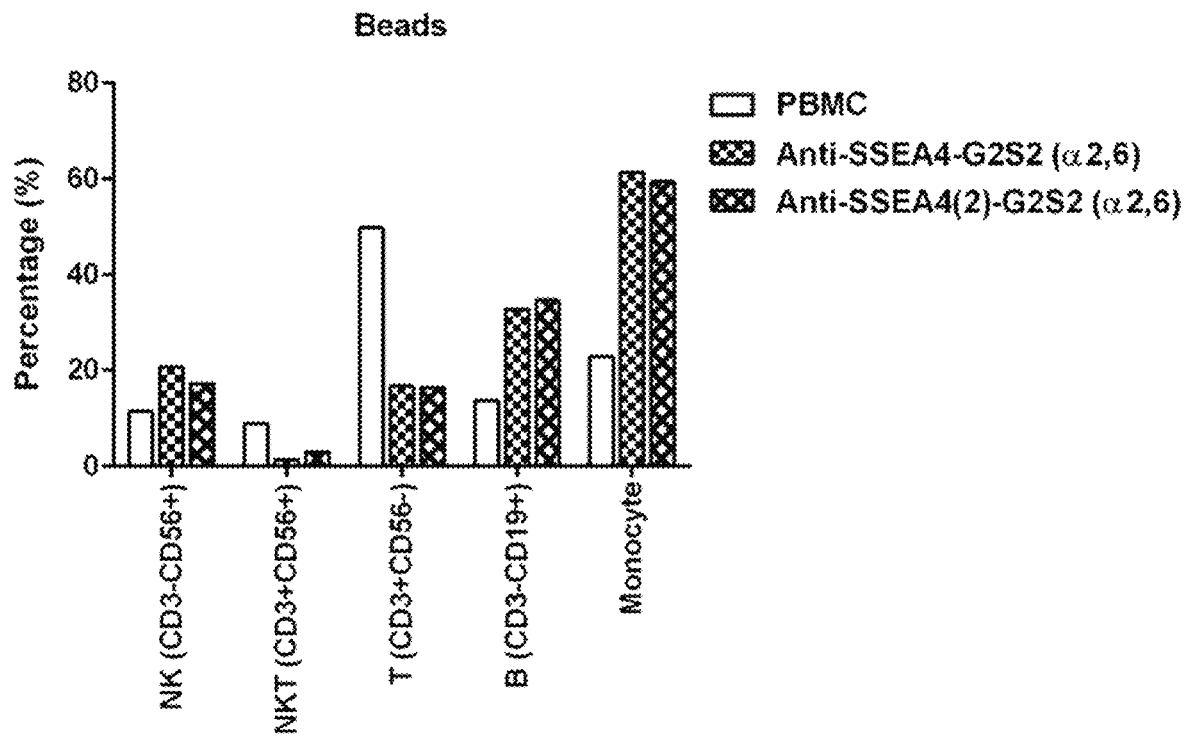
FIG. 12 (A) shows the beads-captured fraction of immune cells enrichment using different antibodies anti-SSEA4-G2S2 (α2,6) and anti-SSEA4(2)-G2S2 (α2,6).
Figure 12:
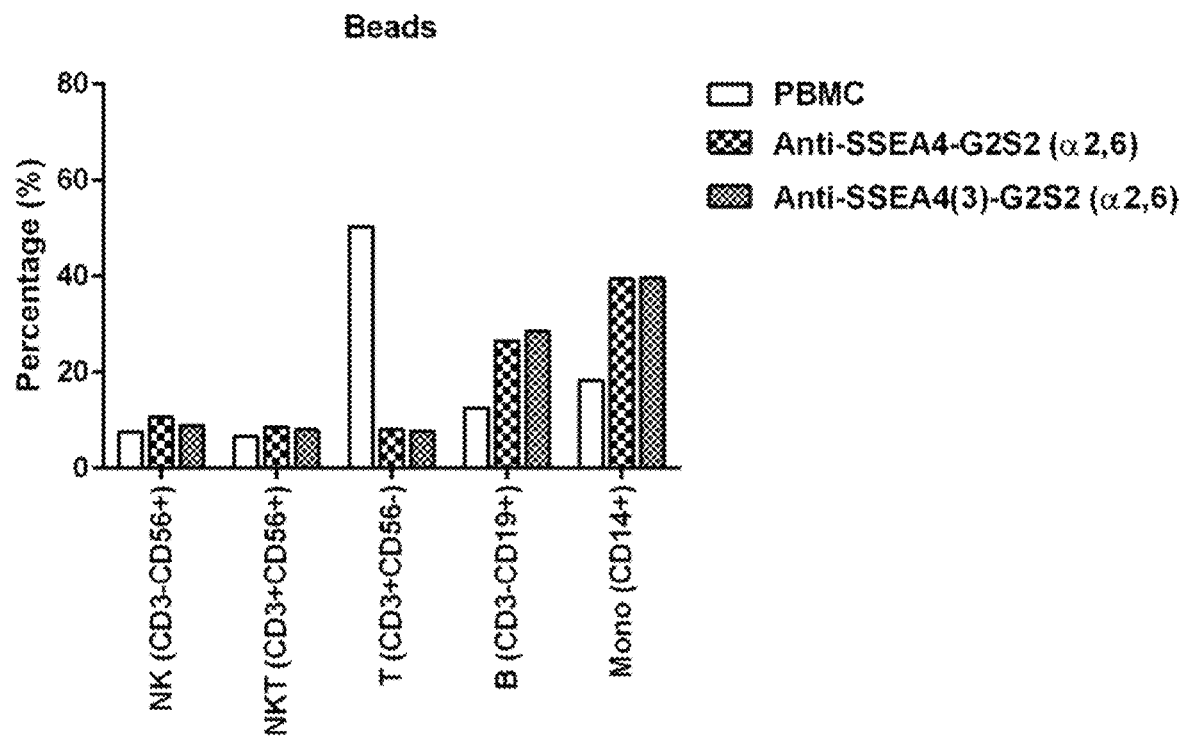
Figure 13:
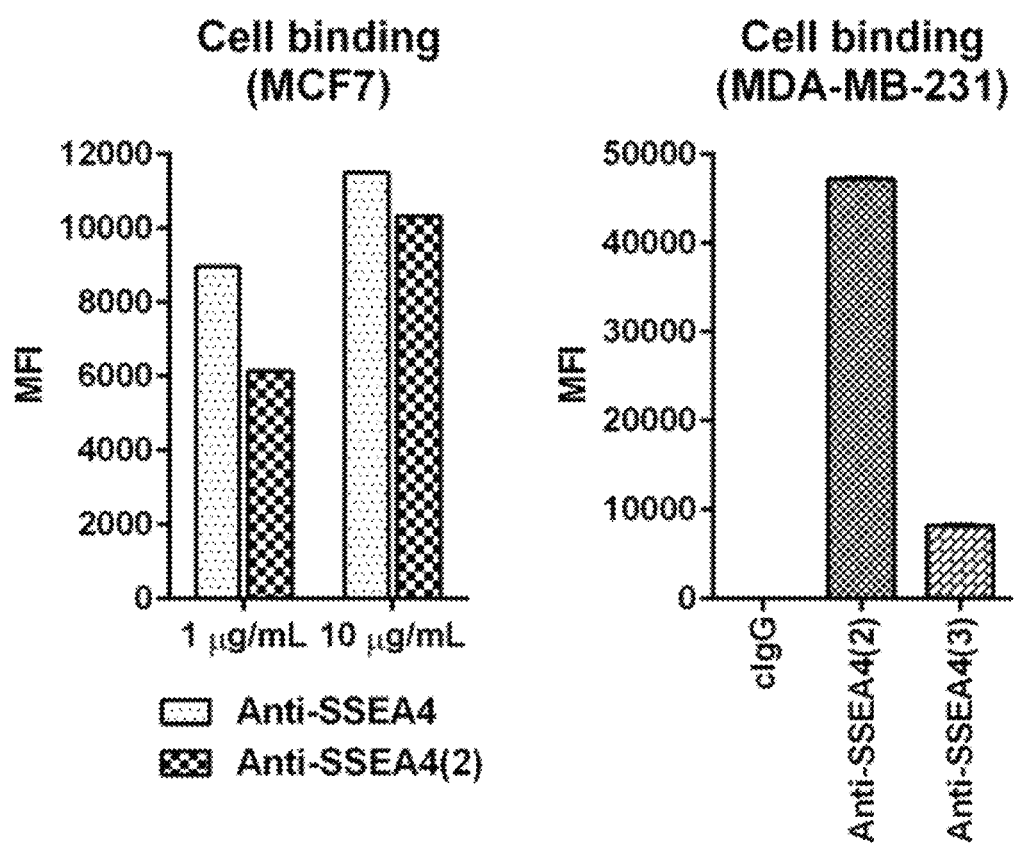
FIG. 13 shows the different cell binding affinities of each anti-SSEA4 antibody used in the immune cells enrichment.
Figure 14:
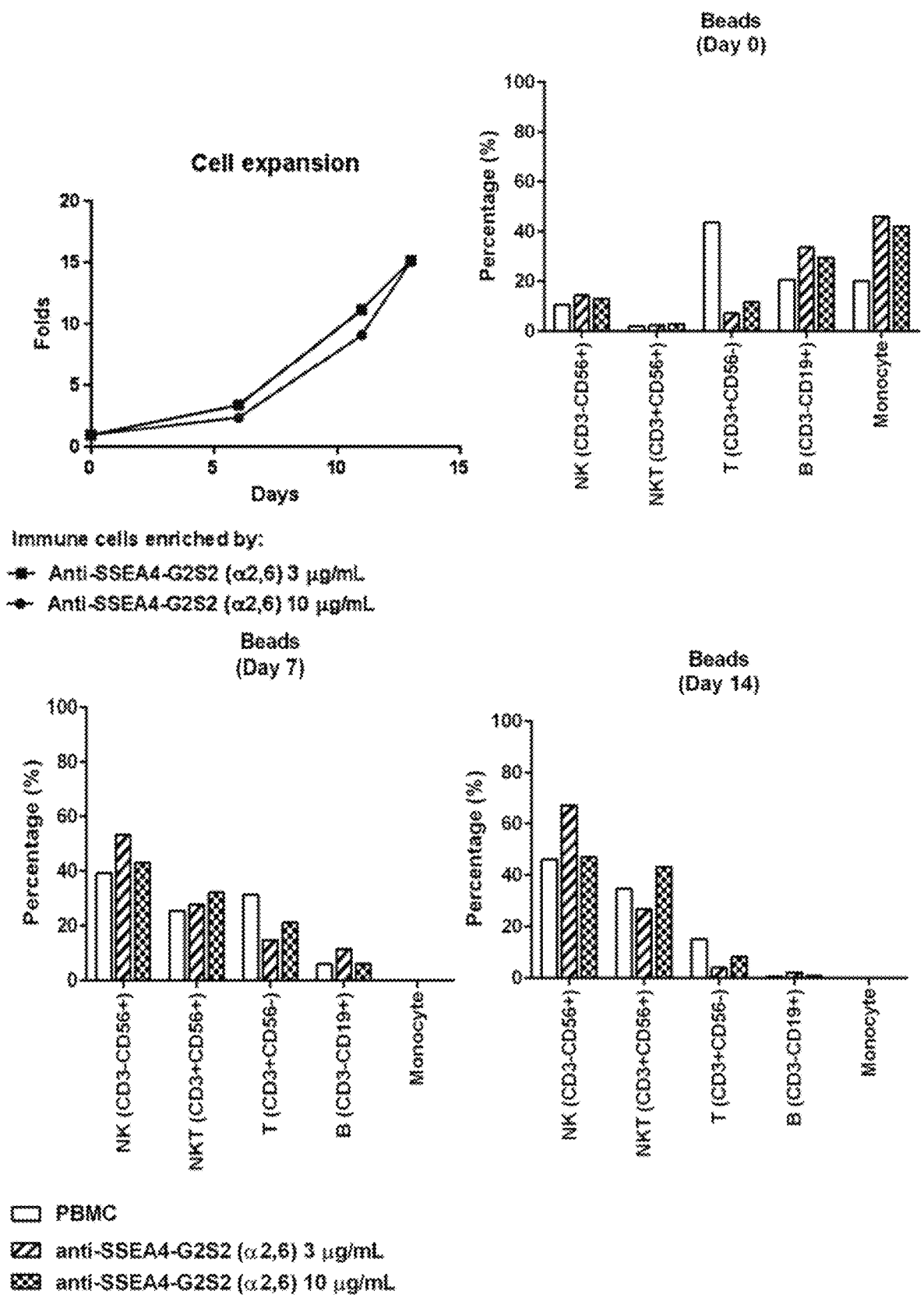
FIG. 14 shows the cell expansion rates and immune cell profiles of captured immune cells after culturing for 7-14 days.
Figure 15:
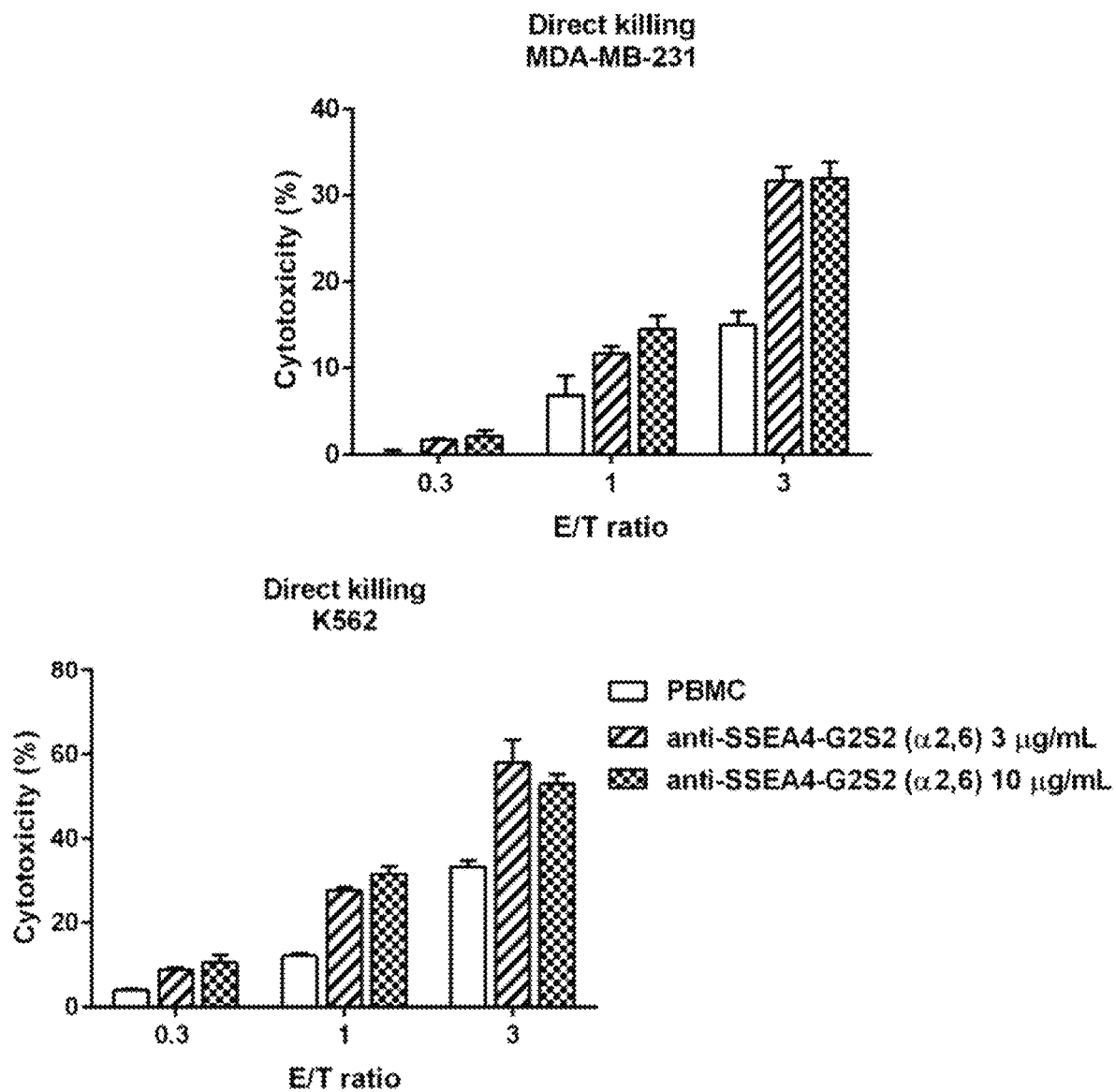
FIG. 15 shows the cytotoxicity of captured cells after culturing for 14 days.
Figure 16:
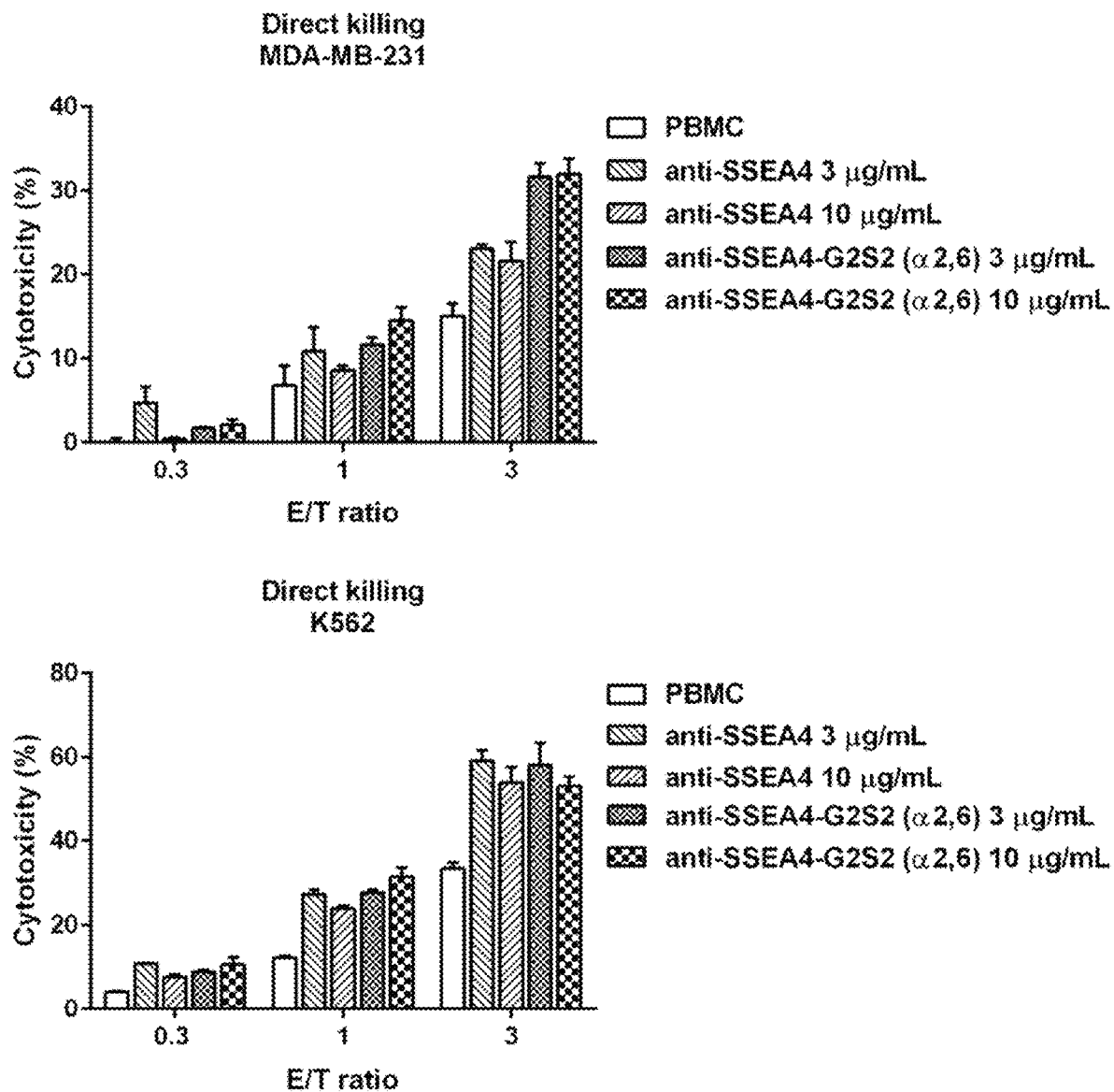
FIG. 16 shows the cytotoxicity of cells captured with parental or glycoengineered antibodies and cultured for 14 days.
Figure 17:
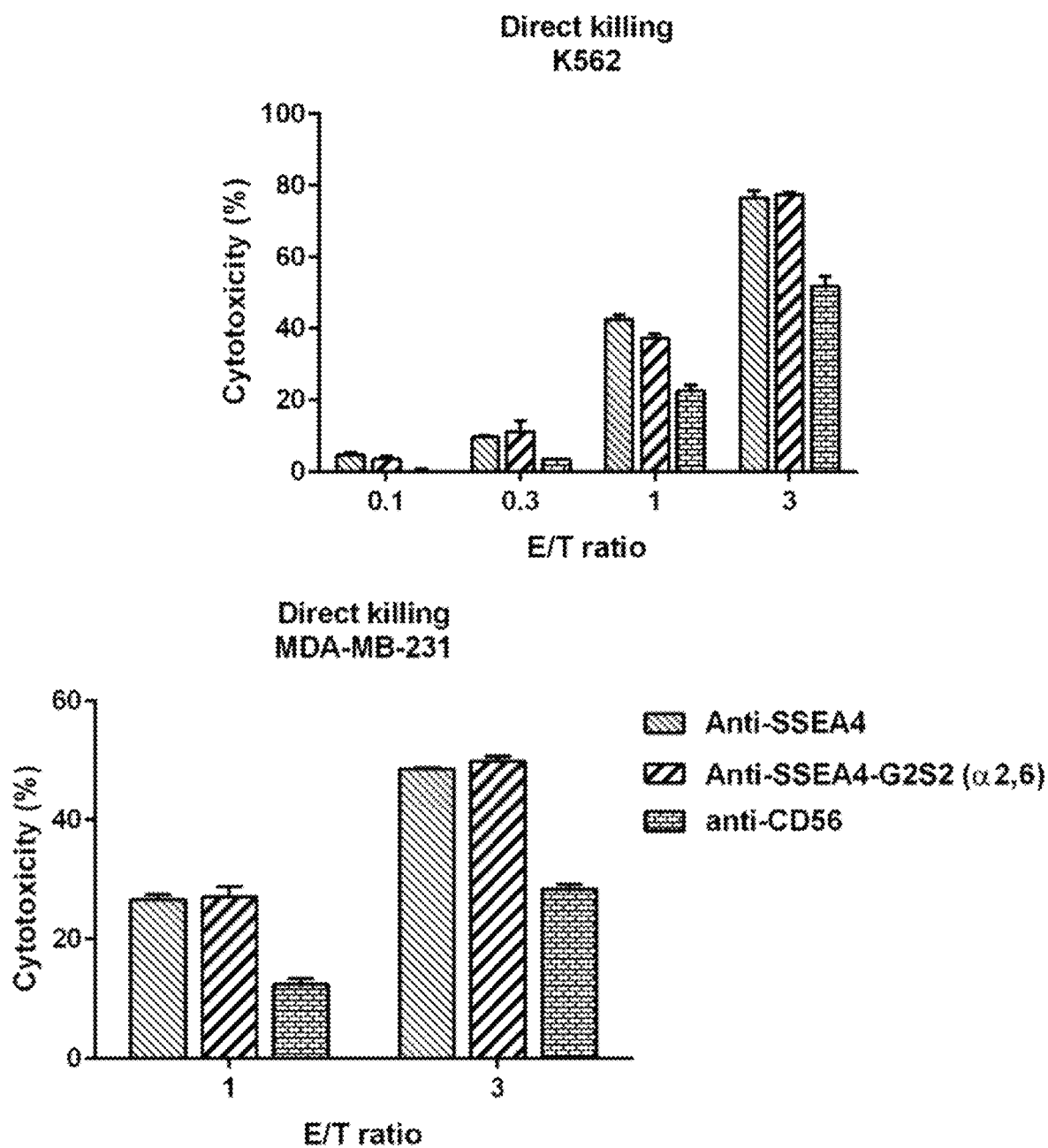
FIG. 17 shows the cytotoxicity of cells captured with the method of the disclosure or with conventional approach using anti-CD56 antibody conjugated beads.
Figure 18:
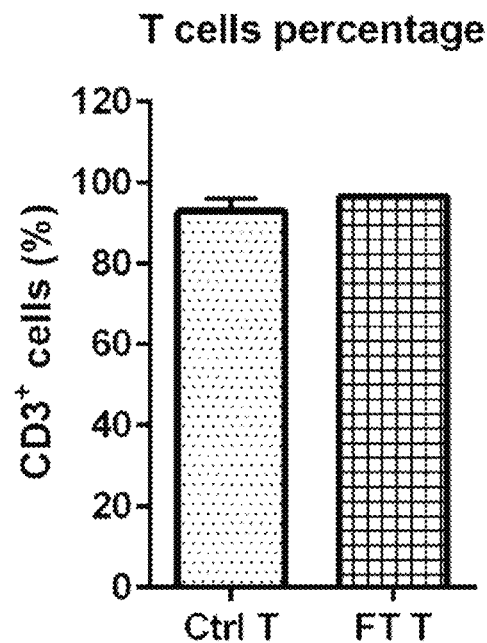
FIG. 18 (A) shows the percentages of T cells ($CD3^+$ cells) isolated with the method of the disclosure (FT T) and the conventional approach (Ctrl T).
Figure 18:
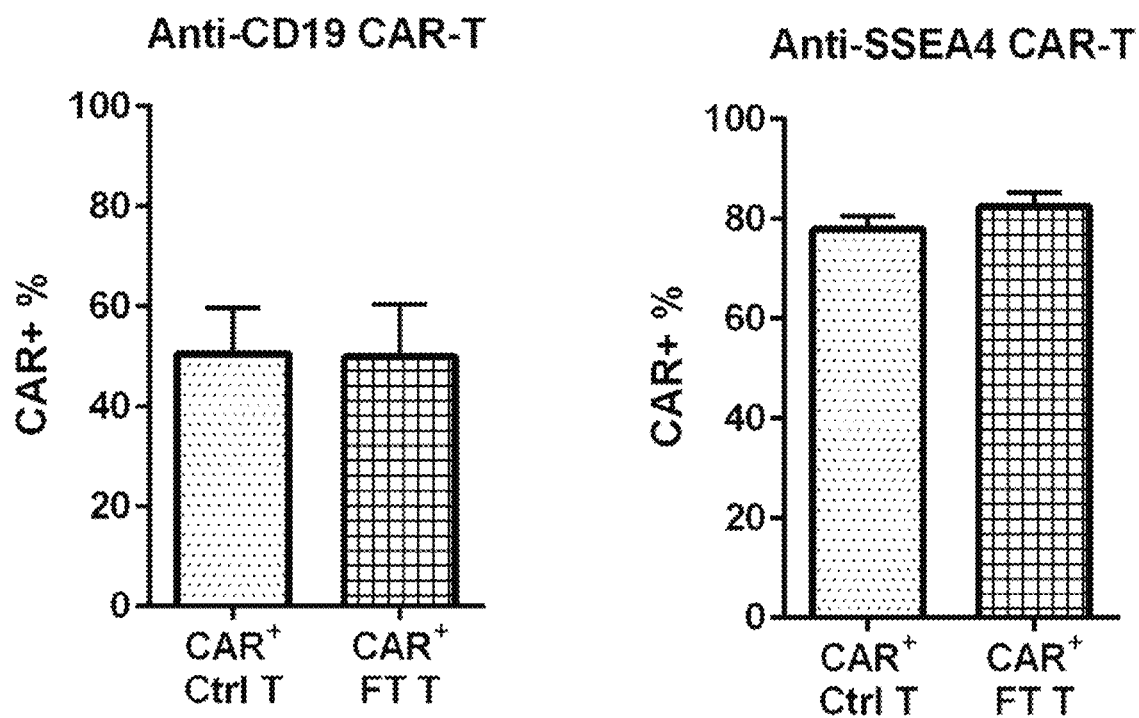
Figure 18:
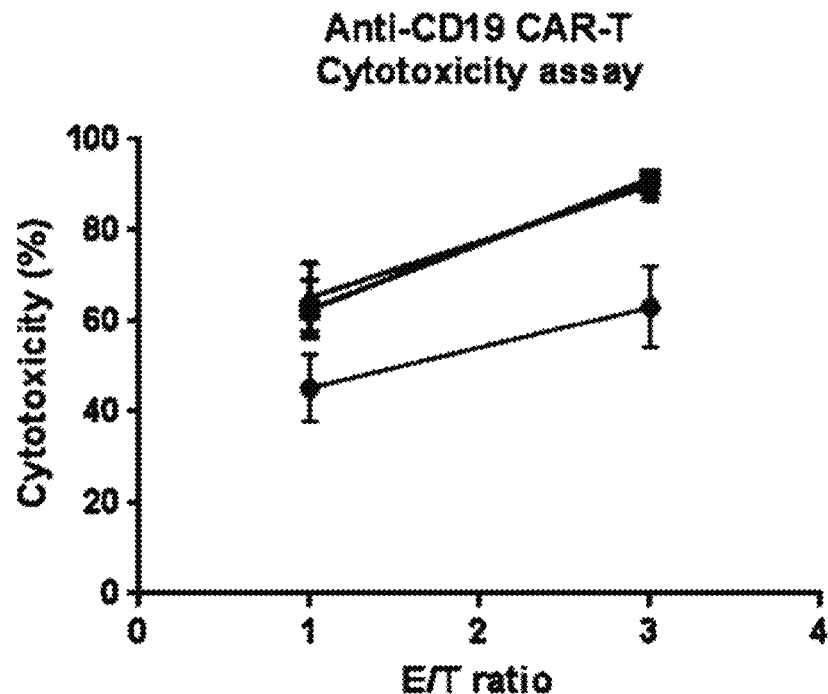
Figure 18:
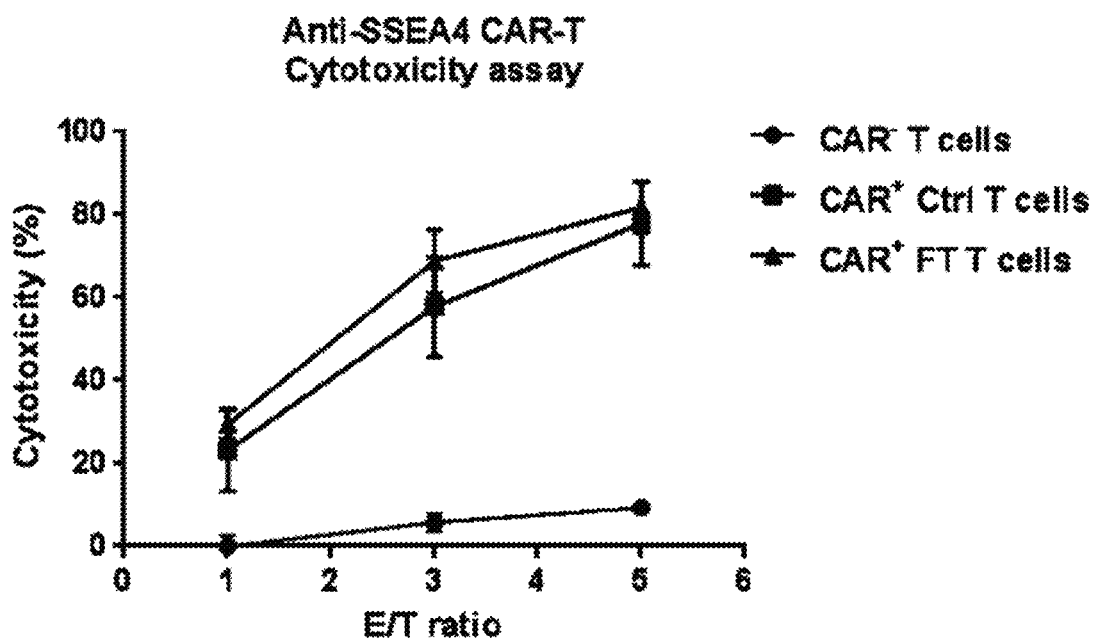

When the method according to the disclosure is applied for the enrichment of the immune cells binding to an Fc region, the antibody or Fc-fused antigen-binding fragment thereof has an Fc region and an Fab region or an antigen-binding fragment, the Fab region or the antigen-binding fragment binds to SSEA4 linked on a support, and the isolated cells bind to the Fc region. The schematic diagram is shown in FIG. 2. It is believed, though not intended to be restricted by any theoretical, the affinity binding between the antigen (SSEA4) and the antibody or antigen-binding fragment thereof causes an antigen binding-induced Fc conformation change. Moreover, SSEA4 and the antibody or antigen-binding fragment thereof according to the disclosure provide good orientation. As a result, a sub-population of immune cells that have high-affinity to the antigen-binding antibody or Fc-fused antigen-binding fragment is enriched. Therefore, the method according to the disclosure provides a high-affinity capture. Furthermore, SSEA4 is very stable and easy synthesized, and the process for linking SSEA4 to the support is easy to perform, and the method according to the disclosure is able to be performed efficiently. In another aspect, the PBMCs except the immune cells to be enriched express neither SSEA4 nor SSEA4 binding molecules, and such fact makes the method according to the disclosure achieves highly specificity.

Not willing limited by theory, it is believed that the glycoengineering according to the disclosure changes the structure of the Fc region and improves the binding to cells with Fc receptors. Therefore, the capture of cells with Fc receptors is easier and more efficient.

The manners for immobilizing the Fab region on the support or linking the SSEA4 to the support may be direct or indirect chemical bonding. In one preferred embodiment of the disclosure, a biotin-streptavidin reaction may be utilized in such immobilization of linkage.

The support according to the disclosure refers to a solid. Examples of the support include but are not limited to a polymer, a metal or a magnetic solid. In one preferred embodiment of the disclosure, the support is a magnetic bead, which benefits the isolating step. Preferably, the diameter of the magnetic bead is less than about 1 µm.

The manner for isolating the cells binding to the antibody or Fc-fused antigen-binding fragment thereof may be varied according to the property of the support. For example, when the support is a magnetic bead, a magnetic force or centrifuge may be applied for such isolation.

In one embodiment of the disclosure, a substantially pure T cell population can be obtained and enriched. In some embodiments of the disclosure, more than about 90% of the cells that fail to bind to the antibody or Fc-fused antigen-binding fragment are T cells. The method further comprises:
  isolating cells that fail to bind to the antibody or Fc-fused antigen-binding fragment thereof.

It is believed, though not intended to be restricted by any theoretical, by removing the cells binding to the antibody or Fc-fused antigen-binding fragment thereof, the cells can be further isolated as a substantially pure T cell population. In order to facilitate the exclusion, the antibody or antigen-binding fragment thereof may be immobilized on a support. In one preferred embodiment of the disclosure, the antibody or antigen-binding fragment is an anti-SSEA4 antibody or SSEA4-binding fragment.

In some embodiments, the antibody or antigen-binding fragment thereof used in the method of the present disclosure is any one of the embodiments describe therein.

In some embodiments of the disclosure, peripheral blood mononuclear cells (PBMCs) are first isolated from a whole blood sample derivated from a subject, and an Fc-enriched population is further obtained by the method or kit for enrichment of cells as disclosed herein. The obtained Fc-enriched population may be further subjected to expansion for therapy/storage uses.

The following examples are provided to aid those skilled in the art in practicing the present disclosure.

EXAMPLES

Example 1: Binding Assay for Anti-SSEA4 Antibodies and Antigen-Binding Fragments scFv-SSEA4 ($V_H$-linker-$V_L$) used herein comprises an anti-SSEA4 heavy chain hMC41 (SEQ ID NO: 23) and light chain (SEQ ID NO: 24) and three copies of G4S linker inbetween.

Fc-fused antigen-binding fragment ($V_H$-linker-$V_L$-Fc) comprises an anti-SSEA4 heavy chain hMC41 (SEQ ID NO: 23), light chain (SEQ ID NO: 24), three copies of G4S linker to inbetween and an Fc region (SEQ ID NO: 38).

A series of mutations of anti-SSEA4 antibodies are also constructed.

Briefly, $2 \times 10^5$ cells were incubated with antibody at concentration of 20 nM in FACS buffer (2% FBS in PBS) at 4° C. for 1 hr. After washes with FACS buffer, cells were then incubated with FITC-conjugated goat anti-human IgG antibody (1:250 diluted in FACS buffer, Jackson Immuno Research) for 30 minutes at 4° C. The detection of anti-SSEA4 antibodies bound to cells was analyzed by BD FACSVerse flow cytometer.

As shown in FIG. 2, scFv-SSEA4-Fc fusion protein (Fc-fused antigen-binding fragment) is able to recognize antigen (SSEA4) on the surface of MCF7 cells as the antibody.

The antigen binding affinity of anti-SSEA4 antibodies were determined by ELISA. Briefly, antibodies were diluted in PBS at concentration of 0.5 mg/mL and then allowed to incubate with SSEA4 in 96-well assay plates for 2 hours at room temperature. Following the wash cycles, HRP-conjugated goat anti-human IgG antibody (1:10,000 diluted in PBS, Jackson Immuno Research) was added to wells and incubated at room temperature for another one hour. After the wash cycles, TMB ELISA substrate (Thermo scientific) was added for color development, and the reaction was stopped by adding equal volume of 2.5N $H_2SO_4$. The absorbance at O.D. 450 nm was read and recorded by M5

ELISA reader (Molecular Device). Position of amino acid changes was presented as wild type amino acid preceding number and mutation following. As shown in in FIGS. 3 to 6, whether a certain amino acid could be substituted was determined by its antigen binding affinity in relative to wild type antibody.

Example 2: Enrichment of Cells

The method for enrichment of cells was carried out as the following scheme.

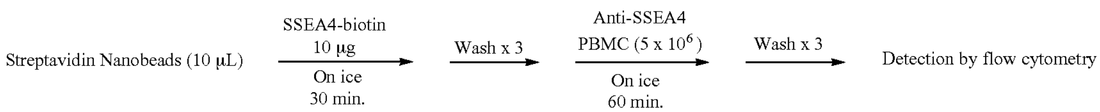

The results of flow cytometry are shown in FIGS. 8 and 9.

Example 3: Comparison of Antibodies With or Without Glycoengineering in Immune Cells Capturing The results of comparison of antibodies with (anti-SSEA4-G2S2 α2,6) or without (anti-SSEA4) glycoengineering in immune cells capturing are shown in FIGS. 10 (flow through) and 11 (beads).

Example 4: Comparison of Different Antibodies With Various Antigen Binding Affinities Using in Immune Cells Capturing The results of comparison of antibodies with (anti-SSEA4-G2S2 α2,6) or (anti-SSEA4(2)-G2S2 α2,6) in immune cells capturing are shown in FIG. 12 (A) (beads).

The results of comparison of antibodies with (anti-SSEA4-G2S2 α2,6) or (anti-SSEA4(3)-G2S2 α2,6) in immune cells capturing are shown in FIG. 12 (B) (beads).

The results of immune cells enrichment using antibodies with different antigen binding affinities and the individual cell binding intensities are shown in FIGS. 12 (A) and 12 (B). It can be seen that the ability of immune cells capturing by the Fc region of anti-SSEA4 antibodies having different Fab regions is substantially the same. The sequence of Fab region would not affect the ability of immune cells capturing by the Fc region.

The results of comparison of antibodies with anti-SSEA4, anti-SSEA4(2) or anti-SSEA4(3) in the individual cell binding intensities are shown in FIG. 13.

It can be seen that the ability of cell binding intensities by the Fc region of anti-SSEA4 antibodies having different Fab regions is different. However, referring to FIGS. 11 and 12 (A), the ability of immune cells capturing by the Fc region would not be altered.

Example 5: Cytotoxicity of the Immune Cells

The captured immune cells were cultured with IL-2 and a feeder cells (inactivated K562) with PRIME-XV medium. The results of cell expansion and profile of cultured cells are shown in FIG. 14, and the results of cytotoxicity of cells on Day 14 are shown in FIG. 15.

The captured immune cells captured by antibodies with (anti-SSEA4-G2S2 α2,6) or without (anti-SSEA4) glycoengineering were cultured with IL-2 and a feeder cells (inactivated K562) with PRIME-XV medium. The results of cytotoxicity on day 14 are shown in FIG. 16.

The captured immune cells captured by antibodies with (anti-SSEA4-G2S2 α2,6) or without (anti-SSEA4) glycoengineering and by anti-CD56 antibodies were cultured with IL-2 and a feeder cells (inactivated K562) with PRIME-XV medium. The results of cytotoxicity on day 14 are shown in FIG. 17.

The results demonstrate that the enriched cells showed better direct killing activity to K562 target cells than parental PBMC or cells enriched by anti-CD56 beads (a general method for isolation of NK cells).

Example 6: Comparison of the Methods for Enrichment of T Cells

The conventional approach for T cell isolation was performed by Miltenyi Biotech Pan T Cell Isolation Kit (Order no. 130-596-535). Non-T cells are labeled with a cocktail of biotin-conjugated monoclonal antibodies and the Pan T Cell MicroBeads Cocktail. The magnetically labeled non-T cells are depleted by retaining them within a magnetic column, while the unlabeled T cells flow through the column.

The method of the disclosure was described below. $5\times10^5$ T cells per well in 12 well plate were spin-inoculated with CAR lentivirus 24 hrs after addition of CD3/CD28 Dynabeads. The virus were added to activated T cells at MOI=10 with 8 mg/mL polybrene and spin at 800 g, 32° C., for 90 minutes. A few hours later, replenish with IL2 containing fresh medium. 4 days after transduction, remove dynabeads. After culturing for ~10 days (expand cells and renew IL2 every 2-3 days), the cells were applied for examination of $CAR^+$ percentage and cytotoxic activity.

In contrast to the T cells isolation with conventional approach (Ctrl T) that requires antibodies cocktails to deplete non-T cells, only one antibody is enough here to obtain pure and high quality of $CD3^+$ T cells. As shown in FIG. 18 (A), similar percentage of $CD3^+$ T cells could be isolated from the flow-through fraction (FT T) with our methodology. In addition, CAR T cells could be prepared from our FT T with comparable percentage (FIG. 18 (B)) and cytotoxic potency (FIG. 18 (C)) to the conventional approach.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A kit, comprising:
   (a) a support;
   (b) a stage-specific embryonic antigen 4 (SSEA4) linked to the support; and
   (c) an antibody or antigen-binding fragment thereof immobilized on the support via binding the Fab region of the antibody or antigen-binding fragment thereof to the SSEA4, wherein the antibody comprises an Fc region or the antigen-binding fragment is fused to an Fc region to form an Fc-fused antigen-binding fragment;
   wherein the antibody or Fc-fused antigen-binding fragment thereof is glycoengineered on the Fc region so that the Fc region consists of N-glycan $Sia_2(\alpha 2\text{-}6)Gal_2GlcNAc_2Man_3GlcNAc_2$ (G2S2 (alpha 2,6 linkage)) such that (i) the antibody or Fc-fused antigen-binding fragment thereof selectively binds to a first fraction of immune cells comprising NK cells, B cells and monocytes in a pool comprising peripheral blood mononuclear cells when the pool is caused to flow through and contact the antibody or antigen-binding fragment thereof immobilized on the support and (ii) a second fraction of immune cells in the pool comprising unbound cells that fail to bind to the antibody or Fc-fused antigen-binding fragment thereof is enriched in T-cells;
   wherein:
   the antibody or antigen-binding fragment thereof comprising the CDRH1 region being SEQ ID NO: 13, the CDRH2 region being SEQ ID NO: 8, the CDRH3 region being SEQ ID NO: 9, the CDRL1 region being SEQ ID NO: 10, the CDRL2 region being SEQ ID NO: 20, and the CDRL3 region being SEQ ID NO: 12;
   the antibody or antigen-binding fragment thereof comprising the CDRH1 region being SEQ ID NO: 13, the CDRH2 region SEQ ID NO: 15, the CDRH3 region being SEQ ID NO: 9, the CDRL1 region being SEQ ID NO: 10, the CDRL2 region being SEQ ID NO: 11, and the CDRL3 region being SEQ ID NO: 12;
   the antibody or antigen-binding fragment thereof comprising the CDRH1 region being SEQ ID NO: 13, the CDRH2 region being SEQ ID NO: 8, the CDRH3 region being SEQ ID NO: 16, the CDRL1 region being SEQ ID NO: 10, the CDRL2 region being SEQ ID NO: 11, and the CDRL3 region being SEQ ID NO: 12;
   the antibody or antigen-binding fragment thereof comprising the CDRH1 region being SEQ ID NO: 14, the CDRH2 region being SEQ ID NO: 8, the CDRH3 region being SEQ ID NO: 18, the CDRL1 region being SEQ ID NO: 10, the CDRL2 region being SEQ ID NO: 11, and the CDRL3 region being SEQ ID NO: 12;
   the antibody or antigen-binding fragment thereof comprising the CDRH1 region being SEQ ID NO: 7, the CDRH2 region being SEQ ID NO: 15, the CDRH3 region being SEQ ID NO: 9, the CDRL1 region being SEQ ID NO: 10, the CDRL2 region being SEQ ID NO: 20, and the CDRL3 region being SEQ ID NO: 12; and
   the antibody or antigen-binding fragment thereof comprising the CDRH1 region being SEQ ID NO: 7, the CDRH2 region being SEQ ID NO: 8, the CDRH3 region being SEQ ID NO: 16, the CDRL1 region being SEQ ID NO: 10, the CDRL2 region being SEQ ID NO: 20, and the CDRL3 region being SEQ ID NO: 12.

2. The kit according to claim 1, wherein the antibody or antigen-binding fragment thereof comprises a CDRH1 region having the amino acid sequence of SEQ ID NO: 13, a CDRH2 region having the amino acid sequence of SEQ ID NO: 8, a CDRH3 region having the amino acid sequence of SEQ ID NO: 9, a CDRL1 region having the amino acid sequence of SEQ ID NO: 10, a CDRL2 region having the amino acid sequence of SEQ ID NO: 20, and a CDRL3 region having the amino acid sequence of SEQ ID NO: 12.

3. The kit according to claim 1, wherein a plurality of the antibodies or Fc-fused antigen-binding fragment thereof are provided in a population, and more than about 90% of the population has the same N-glycan.

4. The kit according to claim 1, wherein the support is a magnetic bead.

5. The kit according to claim 1, wherein the antibody or antigen-binding fragment thereof is an anti-SSEA4 antibody or SSEA4-binding fragment thereof.

6. The kit according to claim 1, wherein the antibody or Fc-fused antigen-binding fragment thereof is constructed and arranged for binding NK cells.

7. The kit according to claim 1, wherein the antibody or Fc-fused antigen-binding fragment thereof is constructed and arranged such that, when a pool comprising peripheral blood mononuclear cells is caused to flow by and contact the antibody or Fc-fused antigen-binding fragment thereof more than 90% of cells that fail to bind to the antibody or Fc-fused antigen-binding are T cells.

* * * * *

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (2)..(2)
<223> OTHER INFORMATION: Xaa being Q, C, D, E, F, G, H, I, L, M, N, P,
      R, S, T, V, W, or Y

<400> SEQUENCE: 1

Ser Xaa Gly Val Tyr
1               5

<210> SEQ ID NO 2
<211> LENGTH: 16
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (2)..(2)
<223> OTHER INFORMATION: Xaa being A, R, N, D, C, E, Q, G, H, I, L, K,
      M, F, S, T, or V

<400> SEQUENCE: 2

Ala Xaa Trp Ala Gly Gly Ser Thr Asn Tyr Asn Ser Ala Leu Met Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (1)..(1)
<223> OTHER INFORMATION: Xaa being V, I, P or S
<220> FEATURE:
<221> NAME/KEY: MISC_FEATURE
<222> LOCATION: (8)..(8)
<223> OTHER INFORMATION: Xaa being N, T, G or Q

<400> SEQUENCE: 3

Xaa Asp Gly Tyr Arg Gly Tyr Xaa Met Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (5)..(5)
<223> OTHER INFORMATION: Xaa being Y or H

<400> SEQUENCE: 4

Ser Ser Val Ser Xaa
1               5

<210> SEQ ID NO 5
<211> LENGTH: 3

```
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (2)..(2)
<223> OTHER INFORMATION: Xaa being A, R, N, C, Q, G, H, I, L, K, M, F,
      S, T, Y, or V

<400> SEQUENCE: 5

Asp Xaa Ser
1

<210> SEQ ID NO 6
<211> LENGTH: 8
<212> TYPE: PRT
<213> ORGANISM: Artificial Sequence
<220> FEATURE:
<223> OTHER INFORMATION: mutant
<220> FEATURE:
<221> NAME/KEY: MISC_FEATURE
<222> LOCATION: (6)..(6)
<223> OTHER INFORMATION: Xaa being Y or I

<400> SEQUENCE: 6

Phe Gln Gly Ser Gly Xaa Pro Leu
1               5

<210> SEQ ID NO 7
<211> LENGTH: 5
<212> TYPE: PRT
<213> ORGANISM: mouse

<400> SEQUENCE: 7

Ser Gln Gly Val Tyr
1               5

<210> SEQ ID NO 8
<211> LENGTH: 16
<212> TYPE: PRT
<213> ORGANISM: mouse

<400> SEQUENCE: 8

Ala Ile Trp Ala Gly Gly Ser Thr Asn Tyr Asn Ser Ala Leu Met Ser
1               5                   10                  15

<210> SEQ ID NO 9
<211> LENGTH: 11
<212> TYPE: PRT
<213> ORGANISM: mouse

<400> SEQUENCE: 9

Val Asp Gly Tyr Arg Gly Tyr Asn Met Asp Tyr
1               5                   10

<210> SEQ ID NO 10
<211> LENGTH: 5
<212> TYPE: PRT
<213> ORGANISM: mouse

<400> SEQUENCE: 10

Ser Ser Val Ser Tyr
1               5

<210> SEQ ID NO 11
<211> LENGTH: 3
```

```
<212> TYPE: PRT
<213> ORGANISM: mouse

<400> SEQUENCE: 11

Asp Thr Ser
1

<210> SEQ ID NO 12
<211> LENGTH: 8
<212> TYPE: PRT
<213> ORGANISM: mouse

<400> SEQUENCE: 12

Phe Gln Gly Ser Gly Tyr Pro Leu
1               5

<210> SEQ ID NO 13
<211> LENGTH: 5
<212> TYPE: PRT
<213> ORGANISM: Artificial Sequence
<220> FEATURE:
<223> OTHER INFORMATION: mutant

<400> SEQUENCE: 13

Ser Ile Gly Val Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: mutant

<400> SEQUENCE: 14

Ser Thr Gly Val Tyr
1               5

<210> SEQ ID NO 15
<211> LENGTH: 16
<212> TYPE: PRT
<213> ORGANISM: Artificial Sequence
<220> FEATURE:
<223> OTHER INFORMATION: mutant

<400> SEQUENCE: 15

Ala Gly Trp Ala Gly Gly Ser Thr Asn Tyr Asn Ser Ala Leu Met Ser
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: mutant

<400> SEQUENCE: 16

Ile Asp Gly Tyr Arg Gly Tyr Asn Met Asp Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: mutant
```

```
<400> SEQUENCE: 17

Val Asp Gly Tyr Arg Gly Tyr Gly Met Asp Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: mutant

<400> SEQUENCE: 18

Val Asp Gly Tyr Arg Gly Tyr Gln Met Asp Tyr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: mutant

<400> SEQUENCE: 19

Ser Ser Val Ser His
1               5

<210> SEQ ID NO 20
<211> LENGTH: 3
<212> TYPE: PRT
<213> ORGANISM: Artificial Sequence
<220> FEATURE:
<223> OTHER INFORMATION: mutant

<400> SEQUENCE: 20

Asp His Ser
1

<210> SEQ ID NO 21
<211> LENGTH: 3
<212> TYPE: PRT
<213> ORGANISM: Artificial Sequence
<220> FEATURE:
<223> OTHER INFORMATION: mutant

<400> SEQUENCE: 21

Asp Val Ser
1

<210> SEQ ID NO 22
<211> LENGTH: 8
<212> TYPE: PRT
<213> ORGANISM: Artificial Sequence
<220> FEATURE:
<223> OTHER INFORMATION: mutant

<400> SEQUENCE: 22

Phe Gln Gly Ser Gly Ile Pro Leu
1               5

<210> SEQ ID NO 23
<211> LENGTH: 119
<212> TYPE: PRT
<213> ORGANISM: Artificial Sequence
<220> FEATURE:
<223> OTHER INFORMATION: mutant

<400> SEQUENCE: 23
```

Gln Val Gln Leu Gln Glu Ser Gly Pro Gly Leu Val Ala Pro Ser Glu
1               5                   10                  15

Thr Leu Ser Ile Thr Cys Thr Val Ser Gly Phe Ser Leu Ser Ser Gln
                20                  25                  30

Gly Val Tyr Trp Val Arg Gln Pro Pro Gly Lys Gly Leu Glu Trp Leu
            35                  40                  45

Gly Ala Ile Trp Ala Gly Gly Ser Thr Asn Tyr Asn Ser Ala Leu Met
50                  55                  60

Ser Arg Leu Ser Ile Ser Lys Asp Asn Ser Lys Ser Gln Val Phe Leu
65                  70                  75                  80

Lys Met Asn Ser Leu Thr Ala Ala Asp Thr Ala Met Tyr Tyr Cys Ala
                85                  90                  95

Arg Val Asp Gly Tyr Arg Gly Tyr Asn Met Asp Tyr Trp Gly Gln Gly
            100                 105                 110

Thr Ser Val Thr Val Ser Ser
            115

<210> SEQ ID NO 24
<211> LENGTH: 107
<212> TYPE: PRT
<213> ORGANISM: Artificial Sequence
<220> FEATURE:
<223> OTHER INFORMATION: mutant

<400> SEQUENCE: 24

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Asn Thr Ser Pro Lys Leu Trp Ile Tyr
            35                  40                  45

Asp Thr Ser Lys Leu Ala Ser Gly Val Pro Gly Arg Phe Ser Gly Arg
50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ser Gly Thr Lys Leu Glu Ile Lys Arg
            100                 105

<210> SEQ ID NO 25
<211> LENGTH: 10
<212> TYPE: PRT
<213> ORGANISM: Artificial Sequence
<220> FEATURE:
<223> OTHER INFORMATION: mutant

<400> SEQUENCE: 25

Gly Phe Ser Leu Lys Asn Tyr Gly Val Ser
1               5                   10

<210> SEQ ID NO 26
<211> LENGTH: 16
<212> TYPE: PRT
<213> ORGANISM: Artificial Sequence
<220> FEATURE:
<223> OTHER INFORMATION: mutant

<400> SEQUENCE: 26

```
Val Ile Trp Gly Asp Gly Ser Thr Asn Tyr His Ser Thr Leu Arg Ser
1               5                   10                  15
```

<210> SEQ ID NO 27
<211> LENGTH: 9
<212> TYPE: PRT
<213> ORGANISM: Artificial Sequence
<220> FEATURE:
<223> OTHER INFORMATION: mutant

<400> SEQUENCE: 27

```
Pro Gly Arg Gly Tyr Ala Met Asp Tyr
1               5
```

<210> SEQ ID NO 28
<211> LENGTH: 10
<212> TYPE: PRT
<213> ORGANISM: Artificial Sequence
<220> FEATURE:
<223> OTHER INFORMATION: mutant

<400> SEQUENCE: 28

```
Ser Ala Ser Ser Ser Val Ser Tyr Met His
1               5                   10
```

<210> SEQ ID NO 29
<211> LENGTH: 8
<212> TYPE: PRT
<213> ORGANISM: Artificial Sequence
<220> FEATURE:
<223> OTHER INFORMATION: mutant

<400> SEQUENCE: 29

```
Tyr Asp Thr Ser Lys Leu Thr Ser
1               5
```

<210> SEQ ID NO 30
<211> LENGTH: 9
<212> TYPE: PRT
<213> ORGANISM: Artificial Sequence
<220> FEATURE:
<223> OTHER INFORMATION: mutant

<400> SEQUENCE: 30

```
Phe Gln Gly Ser Gly Tyr Pro Leu Thr
1               5
```

<210> SEQ ID NO 31
<211> LENGTH: 17
<212> TYPE: PRT
<213> ORGANISM: Artificial Sequence
<220> FEATURE:
<223> OTHER INFORMATION: mutant

<400> SEQUENCE: 31

```
Val Ile Trp Gly Asp Gly Ser Thr Asn Tyr Tyr Ala Asp Ser Val Lys
1               5                   10                  15

Gly
```

<210> SEQ ID NO 32
<211> LENGTH: 9
<212> TYPE: PRT
<213> ORGANISM: Artificial Sequence
<220> FEATURE:
<223> OTHER INFORMATION: mutant

<400> SEQUENCE: 32

```
Pro Gly Ala Gly Tyr Ala Met Asp Tyr
1               5
```

<210> SEQ ID NO 33
<211> LENGTH: 117
<212> TYPE: PRT
<213> ORGANISM: Artificial Sequence
<220> FEATURE:
<223> OTHER INFORMATION: mutant

<400> SEQUENCE: 33

```
Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115
```

<210> SEQ ID NO 34
<211> LENGTH: 107
<212> TYPE: PRT
<213> ORGANISM: Artificial Sequence
<220> FEATURE:
<223> OTHER INFORMATION: mutant

<400> SEQUENCE: 34

```
Gln Ile Val Leu Thr Gln Ser Pro Ala Ile Met Ser Val Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105
```

<210> SEQ ID NO 35
<211> LENGTH: 118
<212> TYPE: PRT
<213> ORGANISM: Artificial Sequence
<220> FEATURE:
<223> OTHER INFORMATION: mutant

<400> SEQUENCE: 35

```
Gln Val Gln Leu Val Glu Ser Gly Gly Val Val Pro Gly Arg
1               5                   10                  15

Ser Leu Arg Leu Ser Cys Thr Val Ser Gly Phe Ser Lys Asn Tyr
            20                  25                  30

Gly Val Ser Trp Val Arg Gln Ala Pro Gly Lys Gly Leu Glu Trp Val
            35                  40                  45

Ala Val Ile Trp Gly Asp Gly Ser Thr Asn Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Ala Gly Tyr Ala Met Asp Tyr Trp Gly Gln Gly Thr
            100                 105                 110

Ser Val Thr Val Ser Ser
            115
```

<210> SEQ ID NO 36
<211> LENGTH: 107
<212> TYPE: PRT
<213> ORGANISM: Artificial Sequence
<220> FEATURE:
<223> OTHER INFORMATION: mutant

<400> SEQUENCE: 36

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
            35                  40                  45

Asp Thr Ser Lys Leu Thr Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Gln Gly Thr Lys Val Glu Ile Lys Arg
            100                 105
```

<210> SEQ ID NO 37
<211> LENGTH: 241
<212> TYPE: PRT
<213> ORGANISM: Artificial Sequence
<220> FEATURE:
<223> OTHER INFORMATION: scFv

<400> SEQUENCE: 37

```
Gln Val Gln Leu Gln Glu Ser Gly Pro Gly Leu Val Ala Pro Ser Glu
1               5                   10                  15

Thr Leu Ser Ile Thr Cys Thr Val Ser Gly Phe Ser Leu Ser Ser Gln
            20                  25                  30

Gly Val Tyr Trp Val Arg Gln Pro Pro Gly Lys Gly Leu Glu Trp Leu
            35                  40                  45

Gly Ala Ile Trp Ala Gly Gly Ser Thr Asn Tyr Asn Ser Ala Leu Met
        50                  55                  60

Ser Arg Leu Ser Ile Ser Lys Asp Asn Ser Lys Ser Gln Val Phe Leu
65                  70                  75                  80
```

```
Lys Met Asn Ser Leu Thr Ala Ala Asp Thr Ala Met Tyr Tyr Cys Ala
                85                  90                  95

Arg Val Asp Gly Tyr Arg Gly Tyr Asn Met Asp Tyr Trp Gly Gln Gly
            100                 105                 110

Thr Ser Val Thr Val Ser Ser Gly Gly Gly Gly Ser Gly Gly Gly Gly
            115                 120                 125

Ser Gly Gly Gly Gly Ser Glu Asn Val Leu Thr Gln Ser Pro Ala Ile
130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Asn Thr Ser
                165                 170                 175

Pro Lys Leu Trp Ile Tyr Asp Thr Ser Lys Leu Ala Ser Gly Val Pro
            180                 185                 190

Gly Arg Phe Ser Gly Arg Gly Ser Gly Asn Ser Tyr Ser Leu Thr Ile
            195                 200                 205

Ser Ser Met Glu Ala Glu Asp Val Ala Thr Tyr Tyr Cys Phe Gln Gly
210                 215                 220

Ser Gly Tyr Pro Leu Thr Phe Gly Ser Gly Thr Lys Leu Glu Ile Lys
225                 230                 235                 240

Arg

<210> SEQ ID NO 38
<211> LENGTH: 233
<212> TYPE: PRT
<213> ORGANISM: Homo sapiens

<400> SEQUENCE: 38

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205
```

```
Phe Ser Cys Ser Val Met His Glu Ala Leu His Asn His Tyr Thr Gln
    210                 215                 220
Lys Ser Leu Ser Leu Ser Pro Gly Lys
225                 230

<210> SEQ ID NO 39
<211> LENGTH: 15
<212> TYPE: PRT
<213> ORGANISM: Artificial Sequence
<220> FEATURE:
<223> OTHER INFORMATION: 3 copies of G4S

<400> SEQUENCE: 39

Gly Gly Gly Gly Ser Gly Gly Gly Gly Ser Gly Gly Gly Gly Ser
1               5                   10                  15
```